United States Patent
Ganesan et al.

(10) Patent No.: US 7,790,832 B2
(45) Date of Patent: *Sep. 7, 2010

(54) METHODS FOR PURIFYING 2-ARYL-3,3-BIS(HYDROXYARYL) PHTHALIMIDINES

(75) Inventors: Balakrishnan Ganesan, Bangalore (IN); Pradeep Jeevaji Nadkarni, Bangalore (IN); Kumar Arun Satyanarayana, Karnataka (IN); Venkata Rama Narayanan Ganapathy Bhotla, Karnataka (IN); Suresh Shanumgam, Bangalore (IN); Gurram Kishan, Bangalore (IN); Ravindra Vikram Singh, Basti (IN)

(73) Assignee: Sabic Innovative Plastics IP B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/849,523

(22) Filed: Sep. 4, 2007

(65) Prior Publication Data

US 2008/0058497 A1   Mar. 6, 2008

Related U.S. Application Data

(62) Division of application No. 11/300,225, filed on Dec. 14, 2005, now Pat. No. 7,563,817.

(51) Int. Cl.
  *C08G 64/00* (2006.01)
  *C08G 63/02* (2006.01)
(52) U.S. Cl. .......... 528/196; 526/64; 528/198; 528/210; 548/467; 548/472
(58) Field of Classification Search ........... 528/196, 528/198, 210; 548/467, 472, 487; 514/415; 526/64

See application file for complete search history.

(56) References Cited

U.S. PATENT DOCUMENTS

| | | | |
|---|---|---|---|
| 4,134,936 A | 1/1979 | Byrne et al. | |
| 4,260,827 A | 4/1981 | Klinkmann et al. | |
| 5,344,910 A | 9/1994 | Sybert | |
| 5,455,310 A | 10/1995 | Hoover et al. | |
| 7,135,577 B2 * | 11/2006 | Rai et al. | 548/472 |
| 7,277,230 B2 * | 10/2007 | Srinivasan et al. | 359/642 |
| 7,329,720 B2 * | 2/2008 | Ganesan et al. | 528/296 |
| 7,365,124 B2 | 4/2008 | Srinivasan et al. | |
| 7,408,016 B2 | 8/2008 | Chatterjee et al. | |
| 2003/0181768 A1 | 9/2003 | O'Young et al. | |
| 2005/0075520 A1 | 4/2005 | O'Young et al. | |
| 2005/0222334 A1 | 10/2005 | Srinivasan et al. | |
| 2008/0033123 A1 * | 2/2008 | Srinivasan et al. | 526/64 |
| 2008/0058597 A1 * | 3/2008 | Arneson et al. | 600/117 |
| 2008/0234496 A1 * | 9/2008 | Xu et al. | 548/487 |

FOREIGN PATENT DOCUMENTS

| EP | 1582549 | * | 10/2005 |
|---|---|---|---|
| EP | 1582549 A1 | | 10/2005 |
| JP | 2820277 B2 | | 3/1991 |

OTHER PUBLICATIONS

Japanese Patent No. JP 03-070790; Publication Date: Mar. 26, 1991; Abstract Only; 1 page.
Japanese Patent No. JP 06-003838; Publication Date: Jan. 14, 1994; Abstract Only; 1 page.
Japanese Patent No. JP 06-082624; Publication Date: Mar. 25, 1994; Abstract Only; 1 page.
Salazkin et al., "Producing Card Biophenols and Some Derivatives Thereof"; Academy of Science; 1976; 26 pages.
International Search Report PCT/US2006/047417; date of mailing; May 7, 2007.
Written Opinion of the International Searching Authority; PCT/US2006/047417; international filing date: Dec. 12, 2006.
M.S. Lin and E.M. Pearce; "Polymers with Improved Flammability Characteristics. I. Phenolphthalein-Related Homopolymers"; Journal of Polymer Science: Polymer Chemistry Edition, vol. 19, 2659-2670 (1981).
M.S. Lin et al., "Thermal Degradation Study of Phenolphthalein Polycarbonate", Journal of Polymer Science: Polymer Chemistry Edition, vol. 19, 2773-2797 (1981).
W.R. Orndorff & R.R. Murray; "A New Class of Phthaleins-Mixed Phthaleins-formed by Heating P-hydroxybenzoyl-o-Benzoic Acid with Phenols"; J. AM. Chem. Soc., vol. 39, 1917, pp. 679-697.

* cited by examiner

*Primary Examiner*—Terressa M Boykin
(74) *Attorney, Agent, or Firm*—Cantor Colburn LLP

(57) ABSTRACT

A method for purifying a 2-aryl-3,3-bis(hydroxyaryl)phthalimidine comprises contacting a crude 2-aryl-3,3-bis(hydroxyaryl)phthalimidine with a purification agent, removing a 2-aryl-3-(aminoaryl)-3-(hydroxyaryl)phthalimidine compound from the crude 2-aryl-3,3-bis(hydroxyaryl)phthalimidine, and producing a purified 2-aryl-3,3-bis(hydroxyaryl) phthalimidine product comprising less than 200 parts per million of the 2-aryl-3-(aminoaryl)-3-(hydroxyaryl)phthalimidine compound. The purification agent is selected from the group consisting of an acidic material, an organic acid chloride, an organic anhydride, or a combination thereof. The 2-aryl-3-(aminoaryl)-3-(hydroxyaryl)phthalimidine compound has a formula:

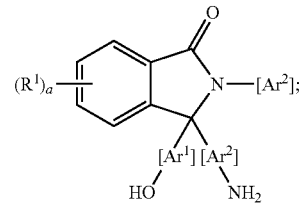

wherein each $R^1$ is independently selected from a group consisting of a hydrocarbyl radical, a nitro radical, and a halogen atom; "a" is an integer from 0 to 4; and $Ar^1$ and $Ar^2$ are independently at each occurrence an aromatic radical. The purified 2-aryl-3,3-bis(hydroxyaryl)phthalimidines have low color, and are useful for preparing polymers, such as polycarbonates having a low color. The polycarbonates are useful for producing articles.

30 Claims, No Drawings

METHODS FOR PURIFYING 2-ARYL-3,3-BIS(HYDROXYARYL) PHTHALIMIDINES

CROSS REFERENCE TO RELATED APPLICATIONS

This application is a divisional of U.S. patent application Ser. No. 11/300,225, filed Dec. 14, 2005, now U.S. Pat. No. 7,563,817 which is fully incorporated herein by reference.

BACKGROUND

The present disclosure generally relates to methods for purifying a 2-aryl-3,3-bis(hydroxyaryl)phthalimidine.

Phenolphthalein derivatives have been used as aromatic dihydroxy compound monomers for preparing polycarbonate polymers as well as polyarylate resins characterized with excellent ductility and high glass transition temperatures. Polycarbonate homopolymers have been prepared by an interfacial polycondensation method using phosgene and 2-hydrocarbyl-3,3-bis(4-hydroxyphenyl)phthalimidine monomers, example, 2-phenyl-3,3-bis(4-hydroxyphenyl)phthalimidine (hereinafter sometimes referred to as "para, para-PPPBP").

Lin and Pearce (Journal of Polymer Science: Polymer Chemistry Edition, (1981) Vol. 19, pp. 2659-2670) reported the synthesis of para, para-PPPBP for preparing polycarbonates and other polymers by refluxing phenolphthalein and aniline hydrochloride in aniline for 6 hours followed by recrystallization from ethanol. During this reaction, side products are created which, if not removed, can result in para, para-PPPBP having an unacceptable color and purity for use as a monomer or as a comonomer. The undesirable side products or impurities generally include both inorganic and organic species. With regard to the manufacture of polycarbonate, the impurities can result in a polymer having a high color, such as a yellowness index of greater than 10; or hinder polymerization and result in low weight average molecular weight polycarbonates, e.g., a number average molecular weight less than about 22,000 Daltons for melt polymerization, which can result in undesirable physical properties to the resulting polymer, such as increased brittleness. Furthermore, the impurities in the para, para-PPPBP monomer can include, for example, trace (parts per million) levels of phenolphthalein and phenolphthalein-derived organic compounds, and/or parts per billion levels of metals that can undesirably produce discoloration in the polycarbonates and other polymers derived therefrom, thereby affecting the transparency of the polymer product. Coloration is not desirable for many commercial applications. U.S. Pat. No. 5,344,910 discloses that copolymers of para, para-PPPBP were found to have poor melt stability resulting in foamy polymer melts and moldings, and discoloration of the resin during the melt processing.

It would therefore be desirable to develop a process for preparing purified 2-aryl-3,3-bis(4-hydroxyaryl)phthalimidines such as the para, para-PPPBP noted above that can be used to produce a polycarbonate having a yellowness index of less than 10. Further, such purified 2-aryl-3,3-bis(4-hydroxyaryl)phthalimidines can then be used for producing polycarbonates and other polymers having improved properties such as a higher number average molecular weight and a yellowness index less than 10.

BRIEF SUMMARY

A method for purifying a 2-aryl-3,3-bis(hydroxyaryl)phthalimidine comprises contacting a crude 2-aryl-3,3-bis(hydroxyaryl)phthalimidine with a purification agent, removing a 2-aryl-3-(aminoaryl)-3-(hydroxyaryl)phthalimidine compound from the crude 2-aryl-3,3-bis(hydroxyaryl)phthalimidine, and producing a purified 2-aryl-3,3-bis(hydroxyaryl) phthalimidine product comprising less than 200 parts per million of the 2-aryl-3-(aminoaryl)-3-(hydroxyaryl)phthalimidine compound. The purification agent is selected from the group consisting of an acidic material, an organic acid chloride, an organic anhydride, or a combination thereof. The 2-aryl-3-(aminoaryl)-3-(hydroxyaryl)phthalimidine compound has a formula:

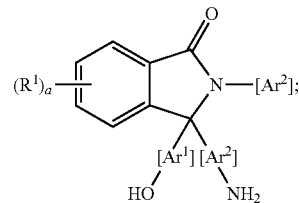

wherein each $R^1$ is independently selected from a group consisting of a hydrocarbyl radical, a nitro radical, and a halogen atom; "a" is an integer from 0 to 4; and $Ar^1$ and $Ar^2$ are independently at each occurrence an aromatic radical. To clarify, when "a" is less than 4, each unsubstituted carbon on the aryl ring is bonded to a hydrogen atom, as is the accepted chemical shorthand. Further structures presented below are similar.

In one embodiment, the acidic material comprises an acidic metal oxide, an acidic organic polymer, an organosulfonic acid having 2 or more carbon atoms, a solution of a mineral acid in a polar organic solvent, an organic acid chloride, an organic anhydride, or combinations of the acidic metal oxide and the acidic organic polymer.

In another embodiment, a method for purifying a 2-aryl-3,3-bis(hydroxyaryl)phthalimidine comprises contacting the 2-aryl-3,3-bis(hydroxyaryl)phthalimidine with an acidic material to produce a pure 2-aryl-3,3-bis(hydroxyaryl)phthalimidine product comprising less than 200 parts per million of a 2-aryl-3-(aminoaryl)-3-(hydroxyaryl)phthalimidine having a formula:

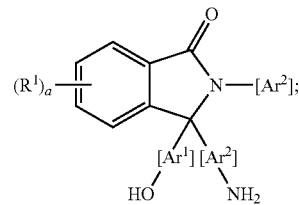

wherein $R^1$ is independently selected from a group consisting of a hydrocarbyl radical, a nitro radical, and a halogen atom; "a" is an integer from 0-4; and $Ar^1$ and $Ar^2$ are independently at each occurrence an aromatic radical; and contacting the pure 2-aryl-3,3-bis(hydroxyaryl)phthalimidine product with a metal oxide adsorbent, to form an ultra-pure 2-aryl-3,3-bis(hydroxyaryl)phthalimidine comprising less than 500 parts per billion of a metal.

A method for preparing a polycarbonate comprising structural units derived from a 2-aryl-3,3-bis(hydroxyaryl)phthalimidine comprises reacting a 2-aryl-3,3-bis(hydroxyaryl)phthalimidine product with a carbonate precursor to produce the polycarbonate comprising structural units derived from the 2-aryl-3,3-bis(hydroxyaryl)phthalimidine product. The 2-aryl-3,3-bis(hydroxyaryl)phthalimidine product comprises at least one member selected from the group consisting of: (A) a pure 2-aryl-3,3-bis(hydroxyaryl)phthalimidine product comprising less than 200 parts per million of a 2-aryl-3-(aminoaryl)-3-(hydroxyaryl)phthalimidine having a formula:

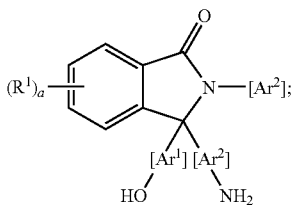

wherein $R^1$ is independently selected from a group consisting of a hydrocarbyl radical, a nitro radical, and a halogen atom; "a" is an integer from 0-4; and $Ar^1$ and $Ar^2$ are independently at each occurrence an aromatic radical; and (B) an ultra-pure 2-aryl-3,3-bis(hydroxyaryl)phthalimidine product comprising less than 200 parts per million of a 2-aryl-3-(aminoaryl)-3-(hydroxyaryl)phthalimidine having a formula:

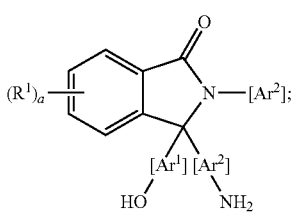

wherein $R^1$ is independently selected from a group consisting of a hydrocarbyl radical, a nitro radical, and a halogen atom; "a" is an integer from 0-4; and $Ar^1$ and $Ar^2$ are independently at each occurrence an aromatic radical; and less than 500 parts per billion of a metal.

In another embodiment, a method for purifying a 2-phenyl-3,3-bis(4-hydroxyphenyl)phthalimidine comprises: contacting a 2-phenyl-3,3-bis(4-hydroxyphenyl)phthalimidine with an acidic material to produce a pure 2-phenyl-3,3-bis(4-hydroxyphenyl)phthalimidine product comprising less than 200 parts per million of a 2-phenyl-3-(4-aminophenyl)-3-(4-hydroxyphenyl)phthalimidine; wherein the acidic material comprises at least one member selected from the group consisting of an acidic metal oxide, an acidic organic polymer, an organosulfonic acid having 2 or more carbon atoms, a solution of a mineral acid in a polar organic solvent, an organic acid chloride, an organic anhydride, and combinations of the acidic metal oxide and the acidic organic polymer.

In another embodiment, a polymer comprises structural units derived from a pure 2-aryl-3,3-bis(hydroxyaryl)phthalimidine product comprising less than 200 parts per million of a 2-aryl-3-(aminoaryl)-3-(hydroxyaryl)phthalimidine having a formula:

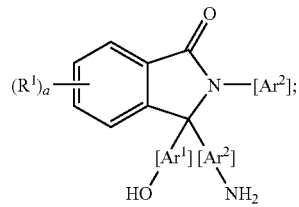

wherein $R^1$ is independently selected from a group consisting of a hydrocarbyl radical, a nitro radical, and a halogen atom; "a" is an integer from 0-4; and $Ar^1$ and $Ar^2$ are independently at each occurrence an aromatic radical.

In yet another embodiment, a polycarbonate comprises structural units derived from a 2-phenyl-3,3-bis(4-hydroxyphenyl)phthalimidine product comprising less than 200 parts per million of 2-phenyl-3-(4-aminophenyl)-3-(4-hydroxyphenyl)phthalimidine; and less than 500 parts per billion of a metal.

Another embodiment of the present disclosure provides a pure 2-aryl-3,3-bis(hydroxyaryl)phthalimidine comprising less than 200 parts per million of a 2-aryl-3-(aminoaryl)-3-(hydroxyaryl)phthalimidine having a formula,

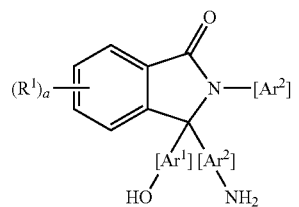

wherein $R^1$ is independently selected from a group consisting of a hydrocarbyl radical, a nitro radical, and a halogen atom; "a" is an integer from 0-4; and $Ar^1$ and $Ar^2$ are independently at each occurrence an aromatic radical.

Still another embodiment of the disclosure provides an ultra-pure 2-aryl-3,3-bis(hydroxyaryl)phthalimidine comprising less than 200 parts per million of a 2-aryl-3-(aminoaryl)-3-(hydroxyaryl)phthalimidine having a formula,

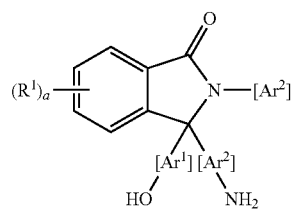

wherein $R^1$ is independently selected from a group consisting of a hydrocarbyl radical, a nitro radical, and a halogen atom; "a" is an integer from 0-4; and $Ar^1$ and $Ar^2$ are independently at each occurrence an aromatic radical; and less than 500 parts per billion of a metal.

In other embodiments, the present disclosure provides for articles comprising the polycarbonates prepared using the 2-aryl-3,3-bis(hydroxyaryl)phthalimidine products.

The above described and other features are exemplified by the following detailed description.

DETAILED DESCRIPTION

In the following description and claims that follow, reference will be made to a number of terms which shall be defined to have the following meanings: the singular forms "a", "an" and "the" include plural referents unless the context clearly dictates otherwise. "Optional" or "optionally" means that the subsequently described event or circumstance may or may not occur, and that the description includes instances where the event occurs and instances where it does not. The terms "formula" and "structure" are used interchangeably herein. The terms "group" and "radical" are sometimes used interchangeably herein.

The term "aliphatic radical" refers to an organic radical having a valence of at least one comprising a linear or branched array of atoms which is not cyclic. The aliphatic radicals comprise at least one carbon atom. Examples of aliphatic radicals include alkyl radicals having 1 to 25 carbon atoms, such as methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof. The array of atoms forming the aliphatic radical may further include heteroatoms such as nitrogen, sulfur, silicon, selenium and oxygen or may be composed exclusively of carbon and hydrogen. The "linear or branched array of atoms which is not cyclic" is intended to include a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, nitro groups and the like. For example, a suitable aliphatic radical is the 4-methylpent-1-yl radical, which is a $C_6$ aliphatic radical comprising a methyl group. Similarly, the 4-nitrobut-1-yl group is a $C_4$ aliphatic radical comprising a nitro functional group. Other suitable aliphatic radicals include a haloalkyl group that comprises one or more halogen atoms which may be the same or different. Suitable halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl; difluorovinylidene; trichloromethyl, bromodichloromethyl, bromoethyl, 2-bromotrimethylene (e.g. —$CH_2CHBrCH_2$—), and the like. Further examples of suitable aliphatic radicals include allyl, carbonyl, dicyanoisopropylidene (—$CH_2C(CN)_2CH_2$—), methyl (—$CH_3$), methylene (—$CH_2$—), ethyl, ethylene, formyl (—CHO), hexyl, hexamethylene, hydroxymethyl (—$CH_2OH$), mercaptomethyl (—$CH_2SH$), methylthio (—$SCH_3$), methylthiomethyl (—$CH_2SCH_3$), methoxy, methoxycarbonyl ($CH_3OCO$—), nitromethyl (—$CH_2NO_2$), thiocarbonyl, vinyl, vinylidene, and the like. By way of further example, a $C_1$-$C_{10}$ aliphatic radical contains at least one but no more than 10 carbon atoms.

The term "aromatic radical" is also sometimes referred herein to as an "aryl radical". The aromatic radical or the aryl radical refers to an array of atoms having a valence of at least one comprising at least one aromatic group. Examples of aryl radicals include those having 6 to 25 carbon atoms, such as ring-substituted and ring-unsubstituted forms of phenyl, tolyl, xylyl, naphthyl, biphenyl, tetraphenyl, and the like; and ring-substituted and ring-unsubstituted forms of benzyl, phenethyl, phenpropyl, phenbutyl, naphthoctyl, and the like. The aromatic radical may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include non-aromatic components. For example, a benzyl group is an aromatic radical that comprises a phenyl ring (the aromatic group) and a methylene group (the non-aromatic component). Similarly a tetrahydronaphthyl radical is an aromatic radical comprising an aromatic group ($C_6H_3$) fused to a non-aromatic component —($CH_2$)$_4$—. The "aromatic radical" can encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, nitro groups, and the like. For example, the 4-methylphenyl radical is a $C_7$ aromatic radical comprising a methyl alkyl group. Similarly, the 2-nitrophenyl group is a $C_6$ aromatic radical comprising a nitro functional group. Suitable aromatic radicals may include halogenated aromatic radicals such as trifluoromethylphenyl, hexafluoroisopropylidenebis(4-phen-1-yloxy) (—OPhC($CF_3$)$_2$PhO—), chloromethylphenyl; 3-trifluorovinyl-2-thienyl; 3-trichloromethylphen-1-yl (3-$CCl_3$Ph-), 4(3-bromoprop-1-yl)phen-1-yl ($BrCH_2CH_2CH_2$Ph-), and the like. Further examples of aromatic radicals include 4-allyloxyphen-1-oxy, 4-benzoylphen-1-yl, dicyanoisopropylidenebis(4-phen-1-yloxy) (—OPhC(CN)$_2$PhO—), 3-methylphen-1-yl, methylenebis (phen-4-yloxy) (—OPh$CH_2$PhO—), 2-ethylphen-1-yl, phenylethenyl, 3-formyl-2-thienyl, 2-hexyl-5-furanyl; hexamethylene-1,6-bis(phen-4-yloxy) (—OPh($CH_2$)$_6$PhO—); 4-hydroxymethylphen-1-yl (4-HOCH$_2$Ph-), 4-mercaptomethylphen-1-yl (4-HSCH$_2$Ph-), 4-methylthiophen-1-yl (4-CH$_3$SPh-), 3-methoxyphen-1-yl, 2-nitromethylphen-1-yl (-PhCH$_2$NO$_2$), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_8$—) represents a $C_7$ aromatic radical.

The term "cycloaliphatic radical" refers to a radical having a valence of at least one and comprising an array of atoms that is cyclic but not aromatic. As defined herein a "cycloaliphatic radical" does not contain an aromatic group and may further include one or more noncyclic components. For example, a cyclohexylmethyl group ($C_6H_{11}CH_2$—) is a cycloaliphatic radical that comprises a cyclohexyl ring (the array of atoms is cyclic but not aromatic) and a methylene group (the noncyclic component). The cycloaliphatic radical may further include heteroatoms such as nitrogen, sulfur, selenium, silicon and oxygen, or may be composed exclusively of carbon and hydrogen. In addition, the cycloaliphatic radical can encompass a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, nitro groups and the like. For example, the 4-methylcyclopent-1-yl radical is a $C_6$ cycloaliphatic radical comprising a methyl group, the methyl group being a functional group which is an allyl group. Similarly, the 2-nitrocyclobut-1-yl radical is a $C_4$ cycloaliphatic radical comprising a nitro group, the nitro group being a functional group. A suitable cycloaliphatic radical may also comprise one or more halogen atoms which may be the same or different. Suitable halogen atoms include, for example; fluorine, chlorine, bromine, and iodine. Suitable cycloaliphatic radicals comprising one or more halogen atoms include 2-trifluoromethylcyclohex-1-yl, 4-bromodifluoromethylcyclooct-1-yl, 2-chlorodifluoromethylcyclohex- 1-yl, hexafluoroisopropylidene-2,2-bis(cyclohex-4-yl) (—$C_6H_{10}C(CF_3)_2C_6H_{10}$—), 2-chloromethylcyclohex-1-yl; 3-difluoromethylenecyclohex-1-yl; 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}$—), and the like. Further examples of cycloaliphatic radicals include 2,2-dicyanoisopropylidenebis(cyclohex-4-yloxy) (—$OC_6H_{10}C(CN)_2C_6H_{10}O$—), 3-methylcyclohex-1-yl, methylenebis(cyclohex-4-yloxy) (—$OC_6H_{10}CH_2C_6H_{10}O$—), 1-ethylcyclobut-1-yl, hexamethylene-1,6-bis(cyclohex-4-yloxy) (—$OC_6H_{10}(CH_2)_6C_6H_{10}O$—); 4-hydroxymethylcyclohex-1-yl (4-$HOCH_2C_6H_{10}$—), 4-mercaptomethylcyclohex-1-yl (4-$HSCH_2C_6H_{10}$—), 4-methylthiocyclohex-1-yl (4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl ($NO_2CH_2C_6H_{10}$—), 4-vinylcyclohexen-1-yl, vinylidenebis(cyclohexyl), and the like.

As defined herein, a purified 2-aryl-3,3-bis(hydroxyaryl) phthalimidine is a material which comprises less than 200 parts per million of an 2-aryl-3-(hydroxyaryl)-3-(aminoaryl) phthalimidine as an impurity. As defined herein, an ultra-pure 2-aryl-3,3-bis(hydroxyaryl)phthalimidine is a material which comprises less than 200 parts per million of an 2-aryl-3-(hydroxyaryl)-3-(aminoaryl)phthalimidine and less than 500 parts per billion of a metal as impurities.

The present disclosure is generally directed to methods for purifying a 2-aryl-3,3-bis(hydroxyaryl)phthalimidine (also referred to herein as "AHP") of formula (I),

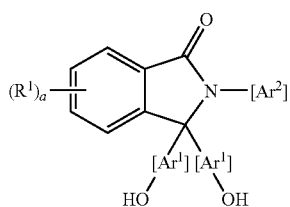

(I)

wherein $R^1$ is independently selected from a group consisting of a hydrocarbyl radical, a nitro radical, and a halogen atom; "a" is an integer from 0-4; and $Ar^1$ and $Ar^2$ are independently at each occurrence an aromatic radical.

The compounds of formula (I) in which the two phenolic OH groups are in the para positions are especially useful as monomers for producing polymers, such as, for example, polycarbonates, polyesters, polyestercarbonates, and the like. An exemplary AHP with the two phenolic OH groups in the para positions is shown in formula (II)

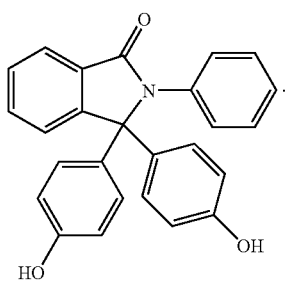

(II)

This particular compound is 2-phenyl-3,3-bis(4-hydroxyphenyl)phthalimidine, i.e., "para, para-PPPBP".

The AHPs can be prepared by the reaction of an aromatic primary amine compound (also sometimes referred to herein as "aryl amine") with a phenolphthalein compound in the presence of an acid catalyst. Suitable aromatic amine compounds are of formula (III):

$Ar^2$—$NH_2$ (III)

wherein $Ar^2$ is an aromatic radical. Aniline is an exemplary aromatic amine.

Suitable phenolphthalein compounds are of formula (IV):

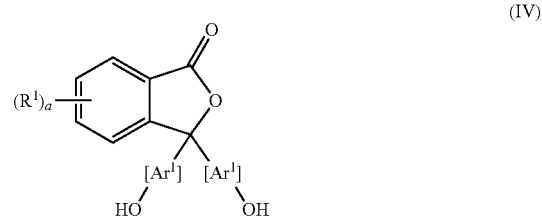

(IV)

wherein $Ar^1$ is an aromatic radical, and $R^1$, and "a" are as previously defined for structure (I).

The acid catalyst is generally used to facilitate formation of the phthalimidine product. Suitable acid catalysts that can be used include amine-acid salts, such as hydrocarbyl amine salts of mineral acids. Examples of suitable mineral acids include hydrochloric acid, sulfuric acid, and the like. Examples of suitable amines include primary, secondary, and tertiary amines having any combination of aliphatic, aromatic, and cycloaliphatic groups bonded to the amine nitrogen. Suitable examples of amine salt catalysts include primary, secondary, and tertiary amine hydrochlorides. Hydrochloride salts of the aromatic primary amines of formula (III) are preferred since these amines also serve as the starting material for preparing the phthalimidines of formula (I). In one embodiment, the catalyst is introduced as a pre-formed salt into the reactor. In another embodiment, the catalyst is generated in situ by first charging the amine into the reactor, and then adding about ⅓ to about 1 part by weight of an appropriate mineral acid to the phenolphthalein of formula (IV). In still another embodiment, about 0.1 parts to about 0.3 parts by weight of hydrogen chloride gas is introduced into a reactor charged with the aryl amine to form an appropriate amount of the aryl amine hydrochloride catalyst. More hydrochloric acid or more hydrogen chloride gas can also used, but is generally not required. A solvent can optionally be employed to form the aryl amine hydrochloride. The solvent can then be removed (if desired), and the aryl amine of formula (III) can be added, followed by addition of the phenolphthalein compound. The reaction of the phenolphthalein compound with the aryl amine proceeds by a condensation reaction to form the desired phthalimidine product. An excess of the aryl amine over the phenolphthalein may be used to keep the reaction proceeding in the forward direction. Likewise, a higher reaction temperature with or without removal of water by-product also facilitates product formation. The use of the aryl amine results in the formation of a 2-aryl-3-(hydroxyaryl)-3-(aminoaryl)phthalimidine (abbreviated herein as "AHAP") by product having a formula (V),

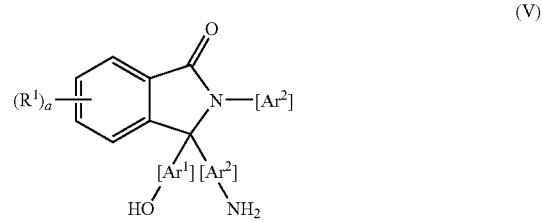

(V)

wherein $R^1$, "a", $Ar^1$, and $Ar^2$ are as previously described. It should be noted that in the structures/formulae for the AHAPs, AHPs, or the phenolphthalein compounds, when the subscript "a" in "$(R^1)_a$" is zero, it denotes a structure where all the $R^1$ substituents are hydrogen atoms. In the case where $R^1$ is other than a hydrogen atom, the subscript "a" can take values from zero to four, with a value of zero for "a" denoting a structure having only hydrogen atoms as the $R^1$ substituents.

In one embodiment, 2-aryl-3,3-bis(hydroxyaryl) phthalimidines have a formula. (VI),

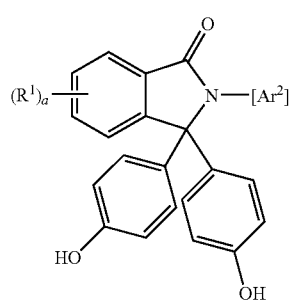

(VI)

wherein $R^1$ "a" and $Ar^2$ are as defined earlier. Compounds of formula (VI) can be prepared by reacting a phenolphthalein compound of formula (VII),

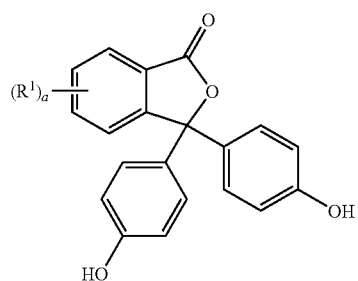

(VII)

wherein $R^1$ and "a" are as defined above; with an aromatic primary amine of formula (III) in the presence of an acidic catalyst. The reaction also produces a 2-aryl-3-(4-hydroxyphenyl)-3-(4-aminoaryl)phthalimidine, i.e., formula (V) in which $Ar^1$ is a 1,4-phenylene radical; and a 2-aryl-3-(4-hydroxyphenyl)-3-(2-hydroxyphenyl)phthalimidine having a formula (VIII),

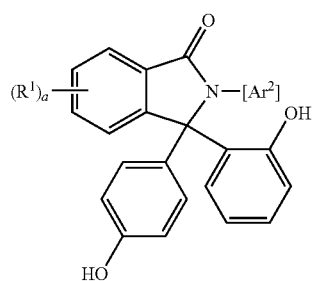

(VIII)

wherein "a", $R^1$ and $Ar^2$ are as defined previously. Note that the structure shown in formula (VIII) is an ortho, para-isomer and is isomeric with the structure shown in formula (VI).

In a specific embodiment, when the phenolphthalein compound is reacted with aniline in the presence of an acid catalyst, the product comprises para, para-PPPBP as the major product, and the compounds 2-phenyl-3-(4-hydroxyphenyl)-3-(4-aminophenyl)phthalimidine (herein abbreviated as "AP") and 2-phenyl-3-(4-hydroxyphenyl)-3-(2-hydroxyphenyl)phthalimidine as minor side products. In general, the formation of AHAP always occurs to a minor extent when preparing the desired AHP. It is desirable to remove the AHAP, particularly since the desired 2-aryl-3,3-bis(4-hydroxyaryl)phthalimidines are valuable as monomers for producing polymers, such as polycarbonates.

The reaction of the phenolphthalein compound with the aromatic primary amine compound generates water as a by-product. In one embodiment, the water by-product can be removed by techniques such as azeotropic distillation. In another embodiment, the reaction mixture can be refluxed without water removal. Water removal can also be achieved, for example, by controlling the reaction temperature such that the water (calculated based on the moles of the phenolphthalein compound, which is preferably the limiting reagent) distills over a period of about 4 hours to 72 hours. If the reaction mixture is heated such that the amount of water by-product distills within a shorter period of time, for example about 6 hours, the phthalimidine product of formula (I) unexpectedly has a relatively greater amount of the AHAP impurity. Therefore, although a higher reaction temperature ensures a quicker consumption of the phenolphthalein compound, it also leads to formation of a higher amount of the AHAP impurity. Thus, in one embodiment, the reaction mixture is heated to a temperature of about 150° C. to about 175° C. to remove water by-product and form the AHP product. In another embodiment, the reaction mixture is heated to a temperature of about 150° C. to about 170° C.

Isolation of the desired AHP from the reaction mixture includes quenching the mixture with an aqueous mineral acid, such as aqueous hydrochloric acid, and precipitating the crude product. The crude AHP product comprises the AHAP impurity as noted above. In one embodiment, the crude material can be used as the feed for the purification process to remove the AHAP impurity. The crude product thus obtained can also be further processed by dissolving in an aqueous inorganic base comprising an alkali metal or alkaline earth metal hydroxide, carbonate, or bicarbonate. Aqueous sodium hydroxide is preferably used. Next, the basic solution thus obtained is treated with a suitable solid adsorbent that can remove color-forming species present in the solution. Activated carbon can be used to remove AHAP. A relatively large amount of activated carbon is generally required to effectively remove AHAP, which results in the generation of a large amount of spent carbon that has to be processed for re-use, or disposed of suitably, which in turn makes the overall purification process less attractive. The AHAP impurity can also be removed by multiple treatments with activated carbon, thus leading to increased unit operations, increased process costs, and decreased recovery of product. Treatment with the activated carbon removes color-forming species present in the solution, Suitable activated carbon include, but are not intended to be limited to, the NORIT series of activated carbon available from Norit Corporation, and those activated carbons commercially available from E. Merck Company. After treatment with the activated carbon, the resulting mixture is filtered to provide a solution that is then treated with an aqueous mineral acid, such as aqueous hydrochloric acid to precipitate AHP. In another embodiment, this precipitated material resulting from aqueous base treatment, followed by treatment with activated charcoal can also be used as the feed for the purification process to remove the AHAP impurity.

If desired, the precipitated material after the charcoal treatment can be stirred with an aliphatic alcohol to remove any trace of the phenolphthalein compound that may still be present and subsequently filtered to provide the 2-aryl-3,3-bis(hydroxyaryl)phthalimidine sample. Suitable aliphatic alcohols include any aliphatic monohydric or dihydric alcohol. Non-limiting examples of suitable aliphatic alcohols include methanol, ethanol, iso-propanol, iso-butanol, n-butanol, tertiary butanol, n-pentanol, iso-pentanol, cyclohexanol, ethylene glycol, propylene glycol, neopentyl glycol and the like. In a particular embodiment, aliphatic monohydric alcohols that are miscible with water, such as methanol, ethanol, and isopropanol are used. Methanol is the preferred aliphatic alcohol for removing the phenolphthalein. The so-produced AHP can also be used as a feed material for the purification step to remove the AHAP impurity. In an embodiment, the AHP produced by the aqueous base treatment, followed by the activated charcoal treatment, and finally the treatment with the alcohol comprises less than 1,000 parts per million of the phenolphthalein starting material relative to an overall weight of the AHP.

In another embodiment, crude AHP product is dissolved in an aqueous base solution, the base solution is treated with the activated carbon and then filtered, and the filtrate is acidified with an aqueous acid to precipitate the AHP, which can be used as a feed material for an additional purification step to remove the AHAP impurity.

The AHAP impurity can be removed from AHP (formula (I)) by contact with an acidic material. The so-purified AHP product comprises less than 200 parts per million of a AHAP. Any suitable acidic material that is capable of interacting with the AHAP impurity so as to remove it from the AHP product can be used. Suitable acidic materials comprise acidic metal oxides, or acidic metal oxides in combination with acidic organic polymers. As defined herein, an acidic metal oxide is a metal oxide comprising Lewis acidic metal oxide sites, Bronsted acidic sites, or any combination of Lewis acidic and Bronsted acidic sites. Lewis acidic metal oxide sites generally arise when the metal atom is coordinatively unsaturated. That is, the metal atom is bonded to electron-withdrawing groups; and therefore can coordinate with donor groups, such as $NH_2$ groups. Bronsted acidic sites in the metal oxide generally comprise acidic groups such as $SO_3H$, $CO_2H$, and OH groups which bridge metal atoms in the metal oxide framework. The acidity of an acidic metal oxide also depends upon other factors, such as the crystal structure of the metal oxide, the mode of preparation, and any pre-treatment steps used to prepare or condition the acidic metal oxide prior to use for purifying the AHP. Without wishing to be bound by any theory, it is believed that the Lewis acidic sites or a combination of the Lewis acidic and Bronsted acidic sites in the metal oxide interact with the amino group of AHAP, thereby removing the AHAP present in the AHP product.

The AHAP impurity can be removed from AHP (formula (I)) by contact with an acidic material. The so-purified AHP product comprises less than 200 parts per million of an AHAP. Any suitable acidic material that is capable of interacting with the AHAP impurity so as to remove it from the AHP product can be used. The acidic material can be acetic acid. Suitable acidic materials comprise acidic metal oxides, or acidic metal oxides in combination with acidic organic polymers. As defined herein, an acidic metal oxide is a metal oxide comprising Lewis acidic metal oxide sites, Bronsted acidic sites, or any combination of Lewis acidic and Bronsted acidic sites. Lewis acidic metal oxide sites generally arise when the metal atom is coordinatively unsaturated. That is, the metal atom is bonded to electron-withdrawing groups; and therefore can coordinate with donor groups, such as $NH_2$ groups. Bronsted acidic sites in the metal oxide generally comprise acidic groups such as $SO_3H$, $CO_2H$, and OH groups which bridge metal atoms in the metal oxide framework. The acidity of an acidic metal oxide also depends upon other factors, such as the crystal structure of the metal oxide, the mode of preparation, and any pre-treatment steps used to prepare or condition the acidic metal oxide prior to use for purifying the AHP. Without wishing to be bound by any theory, it is believed that the Lewis acidic sites or a combination of the Lewis acidic and Bronsted acidic sites in the metal oxide interact with the amino group of AHAP, thereby removing the AHAP present in the AHP product.

The acidic metal oxide may also be pre-treated with a suitable agent prior to contacting with the AHAP feed. Pre-treatment is generally done with an aqueous solution of a mineral acid (inorganic acid), such as for example, aqueous hydrochloric acid. The pre-treatment is done to remove trace levels of leachable metals that may be present in the acidic metal oxide. Acidic metal oxides, such as acidic alumina and acidic silica can be pre-treated prior to contacting with the AHAP feed.

The acidic organic polymer can be any organic polymer comprising at least one Bronsted acidic functional group. Bronsted acidic functional groups are exemplified by sulfonic acid groups, carboxylic acid group, phosphorus-based acidic groups comprising one or more P—OH bonds, and the like. Non-limiting examples of acidic organic polymers include poly(styrenesulfonic acid), poly(vinylsulfonic acid), poly(vinylphosphonic acid), and the like. Homopolymers and copolymers of these acidic organic polymers can be used. In some cases, the acidic organic polymer can be used as a solution in a suitable solvent, such as water. Generally, however, it is preferable to use the acidic organic polymer in an insoluble form for removing AHAP from AHP. Cross-linked acidic organic polymers are generally insoluble and can be used. Suitable insoluble acidic organic polymers include the well-known acidic ion exchange resin class of materials. These materials generally comprise a sulfonated product of a polystyrene that is cross-linked with divinylbenzene. Thus, any of the sulfonated polystyrene resins comprising up to 20 weight percent of divinylbenzene, relative to an overall weight of the resin can be used. More specifically, the acidic ion exchange resin is a sulfonated polystyrene resin crosslinked with up to about 4 weight percent of divinylbenzene relative to an overall weight of the resin.

Acidic materials that have both Lewis acidic and Bronsted acidic sites can remove both the AHAP impurity as well as trace levels of metals present in the AHP feed. Without wishing to be bound by any theory, it is believed that the Bronsted acid sites interact with the amino group in AHAP, whereas the Lewis acid sites interact and bind the metals. Thus, in one embodiment, acidic materials such as the acidic metal oxides, which may contain both types of acidic sites can remove both impurities. In another embodiment, the acidic material for removing AHAP and trace levels of metals from AHP comprises an acidic metal oxide and an insoluble acidic organic polymer, such as for example, the ion exchange resins, described above.

Removal of AHAP from AHP feed can also be achieved by using an organosulfonic acid, preferably those having 2 or more carbon atoms. Examples of such organosulfonic acids include ethanesulfonic acid, propanesulfonic acid, butanesulfonic acid, octanesulfonic acid, dodecylbenzenesulfonic acid, and the like. Combinations of sulfonic acids can also be used. An organic solvent is generally used with the organosulfonic acids.

Another method to remove the AHAP impurity from an AHP feed is by contacting the AHP with a solution of a mineral acid in a polar organic solvent. Suitable mineral acids include hydrochloric acid, phosphoric acid, and the like. Mixtures of mineral acids can also be used. Sulfuric acid was generally found to be less effective. Suitable organic solvents comprise at least one functional group selected from the group consisting of a hydroxy group, a ketone carbonyl group, a carboxylic acid group, an ester group, a sulfoxide group, a nitrile group, an ether group, and a nitro group. Organic solvents that comprise at least one member selected from the group consisting of an organic hydroxy compound, an organic ketone, an organic amide, an organic sulfoxide, an organic ether, and an organic nitrile can be used. Each of these categories of solvents may further comprise more than one functional group, which may be the same or different from the other functional group(s). For example ethanol, ethylene glycol, and 2-ethoxyethanol may be used, either individually, or in any relative proportion, as suitable organic solvents. In one embodiment, aliphatic alcohols having at least one hydroxy group can be used as the organic solvent. Suitable organic hydroxy compounds include aliphatic, cycloaliphatic and aromatic hydroxy compounds having at least one hydroxy group. The aliphatic hydroxy compounds include linear and branched aliphatic mono-hydroxy compounds, non-limiting examples of which are methanol, ethanol, isopropanol, n-butanol, sec-butanol, iso-butanol, tert-butanol, and the like. Mixtures of these compounds can also be used. Aliphatic dihydroxy compounds, such as the glycols, exemplified by ethylene glycol, propylene glycol, and the like may also be used. Non-limiting examples of aromatic hydroxy compounds include phenol, ortho-cresol, benzyl alcohol, and the like. Some examples of cycloaliphatic hydroxy compounds include cyclopentanol, cyclohexanol, cyclohexanediol, and the like. In an embodiment, suitable organic hydroxy compounds include methanol, isopropanol, or any combination of methanol and isopropanol. Methanol is an exemplary organic solvent for use with a mineral acid to remove trace levels of metals from AHP. Organic ketones suitable for use as the organic solvent include acetone, 2-butanone, methyl ethyl ketone, diethyl ketone, methyl isopropyl ketone, and the like. In an embodiment, the organic solvent comprises acetone. Organic sulfoxides that may be used as the organic solvent include dimethylsulfoxide, methyl ethyl sulfoxide, diethyl sulfoxide, and the like. Non-limiting examples of organic nitriles include the aliphatic nitriles, such as acetonitrile, propionitrile, butyronitrile, hexanedinitrile, and the like. Examples of organic nitro compounds that may be used include nitromethane, nitroethane, and the like. In an embodiment, the organic solvent is selected from the group consisting of methanol, ethanol, isopropanol, sec-butanol, phenol, acetone, butanone, formamide, 2-ethoxyethanol, and dimethylsulfoxide.

The AHAP impurity in AHP can also be removed by reacting it out with an organic anhydride. Some examples of organic anhydrides include phthalic anhydride, acetic anhydride, propionic anhydride, malonic anhydride, and the like. In embodiment, the weight ratio of the organic anhydride to the feed AHP is from about 1:1 to about 1:0.01, respectively.

Organic acid chlorides can also be used to remove AHAP impurity from an AHP. The amino group of the AHAP selectively reacts with the organic acid chloride, thereby facilitating the purification.

If the feed AHP material contains the phenolphthalein compound, the phenolphthalein compound can remain in the AHP obtained after removal of the AHAP by treatment with the acidic material. In such cases, the AHP obtained can be further treated with a polar solvent, such as an aliphatic alcohol to remove the phenolphthalein impurity. But if as discussed earlier, the feed AHP material is one that has already been treated with a polar solvent to remove the phenolphthalein compound, treatment with the acidic material will directly furnish the pure AHP.

Metal oxides are effective for removing trace levels of metal impurities from the AHP feed. Typically, the AHP feed contains trace levels of metals such as iron, calcium, zinc, sodium, aluminum, chromium, nickel, manganese, potassium, and the like. In some cases, the metals can originate from the process used for producing the phenolphthalein compound, as it is well known that the reaction requires a Lewis acid catalyst such as zinc chloride, aluminum chloride, iron chloride, and the like. Treatment of the AHP with metal oxides brings the residual level of each of these metals to less than 500 parts per billion. The metal oxides encompass the basic, neutral, and acidic metal oxides. Examples of basic metal oxides include for example, the various grades of basic alumina available commercially. Non-limiting examples of neutral metal oxides include neutral silica and neutral alumina. Acidic metal oxides, such as those described above are particularly useful for removing the metal impurities from the AHP feed. The AHP feed can either be the crude AHP obtained directly from the reaction of the phenolphthalein compound and the aromatic amine, or it can be the pure AHP obtained from the treatment process described previously. The activity of the metal oxide to remove the metal impurities depends upon the temperature, and a lower temperature generally gives a better activity. The temperature can be in a range from ambient to about 70° C. in an embodiment. Temperatures in the range from about 40° C. to about 60° C. are desirable. Polar organic solvents with or without water as a co-solvent can be used to prepare the solution of the feed for the treatment with the metal oxides. Some examples of suitable solvents include isopropanol, methanol, ethanol, acetone, 90:10 (volume/volume) of isopropanol/water, 80:20 (volume/volume) isopropanol/water, 90:10 (volume/volume) of phenol/water, 90:10 (volume/volume) of acetone/water, and the like.

The purified AHP thus obtained after treatment with the acidic material comprises less than 200 parts per million (abbreviated as "ppm") of AHAP in one embodiment, and less than 50 ppm in another embodiment. When an acidic material that is capable of removing both the AHAP impurity and trace metals impurities is used, the purified AHAP thus obtained has less 200 ppm of the AHAP and less than 500 parts per billion (abbreviated as "ppb") of a metal impurity in one embodiment, and less than 50 ppm of the AHAP and less than 500 ppb of a metal impurity in another embodiment. Advantageously, an AHP which has less than 500 ppb of a metal impurity can be polymerized by a melt polymerization method, which is generally sensitive to the levels of metal impurities present in the polymerization reaction mixture. In one embodiment, polymers prepared using the purified AHP have a yellowness index of less than 20 in an embodiment, and less than 10 in another embodiment, as measured in chloroform solutions using ASTM E 313-00 (previously called D1925 test method) test method, published in February 2001.

The purified AHPs and the ultra-pure AHPs are commercially valuable monomers or comonomers for producing a variety of polymers and polymer compositions. These polymers and polymer compositions can be formed by reactions of the phenolic OH groups of the AHPs. For example, the AHPs can be reacted either by themselves, or with one or more other aromatic dihydroxy compounds, together with a carbonic acid diester (also sometimes called as a carbonate ester in the present disclosure) such as diaryl carbonate or carbonyl halide to form polycarbonate. Thus, the AHPs can react in the same way as any aromatic dihydroxy compound, such as for example, a bisphenol A would.

In one embodiment, AHPs in which the two phenolic OH groups are in the para position relative to the phthalimidine ring carbon may also comprise varying amounts of the corresponding ortho, para AHP isomer. The level of the ortho, para-AHP can be below 1000 ppm in the para, para-AHP monomer to be polymerized. In some instances, a high level of the ortho, para-AHP may be unacceptable for producing polymers having a high molecular weight. Without wishing to be bound by any theory, it is believed an ortho-phenolic OH group in an ortho, para-AHP may hinder the rate of polymerization, thereby resulting in a polymer having a relatively lower molecular weight. Suitable polymers that can be produced from the AHPs include, but are not limited to homopolymers and copolymers of a polycarbonate, a polyestercarbonate, a polyester, a polyesteramide, a polyimide, a polyetherimide, a polyamideimide, a polyether, a polyethersulfone, a polycarbonate-polyorganosiloxane block copolymer, a copolymer comprising aromatic ester, estercarbonate, and carbonate repeat units; and a polyetherketone. A suitable example of a copolymer comprising aromatic ester, estercarbonate, and carbonate repeat units is the copolymer produced by the reaction of a hydroxy-terminated polyester, such as the product of reaction of isophthaloyl chloride, and terephthaloyl chloride with resorcinol, with phosgene and an aromatic dihydroxy compound, such as bisphenol A. In one embodiment, polycarbonates are prepared using the AHPs of formula (I) wherein $R^1$, "a", $Ar^1$, and $Ar^2$ are as previously defined.

In one embodiment, polycarbonates having desirable properties are synthesized, wherein the polycarbonates include structural units of formula (IX),

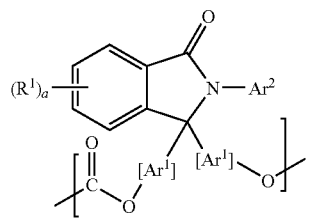

(IX)

wherein $R^1$, "a", $Ar^1$ and $Ar^2$ are as defined previously for formula (I); and the C=O structural units are derived from a C=O donor, such as phosgene or a carbonic acid diester.

The polycarbonate composition may further comprise structural units derived from at least one other aromatic dihydroxy compound such as is represented by the general formula (X),

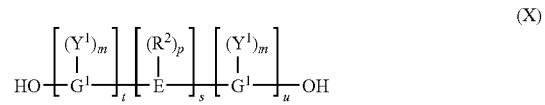

(X)

wherein each $G^1$ is an independently aromatic group; E is selected from the group consisting of an alkylene group, an alkylidene group, a cycloaliphatic group, a sulfur-containing linkage group, a phosphorus-containing linkage group, an ether linkage group, a carbonyl group, a tertiary nitrogen group, and a silicon-containing linkage group; $R^2$ is independently at each occurrence a hydrogen atom or a monovalent hydrocarbyl group; $Y^1$ is independently at each occurrence selected from the group consisting of a monovalent hydrocarbyl group, an alkenyl group, an allyl group, a halogen, an oxy group and a nitro group; each m is independently a whole number from zero through the number of positions on each respective $G^1$ available for substitution; p is a whole number from zero through the number of positions on E available for substitution; t is a natural number greater than or equal to one; s is either zero or one; and u is a whole number.

Suitable examples of E include cyclopentylidene, cyclohexylidene, 3,3,5-trimethylcyclohexylidene, methylcyclohexylidene, 2-[2.2.1]-bicycloheptylidene, neopentylidene, cyclopentadecylidene, cyclododecylidene, and adamantylidene; a sulfur-containing linkage such as sulfide, sulfoxide or sulfone, a phosphorus-containing linkage such as phosphinyl, phosphonyl, an ether linkage, a carbonyl group, a tertiary nitrogen group, and a silicon-containing linkage such as a silane or siloxy linkage.

In the aromatic dihydroxy comonomer compound shown in Formula (X), when more than one $Y^1$ substituent is present, they may be the same or different. The same holds true for the $R^2$ substituent. Where "s" is zero in formula (X) and "u" is not zero, the aromatic rings are directly joined with no intervening alkylidene or other bridge. The positions of the hydroxyl groups and $Y^1$ on the aromatic nuclear residues $G^1$ can be varied in the ortho, meta, or para positions and the groupings can be in vicinal, asymmetrical or symmetrical relationship, where two or more ring carbon atoms of the hydrocarbon residue are substituted with $Y^1$ and hydroxyl groups. In some embodiments, the parameters "t", "s", and "u" are each one; both $G^1$ radicals are unsubstituted phenylene radicals; and E is an alkylidene group such as isopropylidene. In particular embodiments, both $G^1$ radicals are p-phenylene, although both may be ortho- or meta-phenylene or one ortho- or meta-phenylene and the other para-phenylene.

Some illustrative, non-limiting examples of aromatic dihydroxy compounds of formula (X) include 2,4'-dihydroxydiphenylmethane, bis(2-hydroxyphenyl)methane, bis(4-hydroxyphenyl)methane, bis(4-hydroxy-5-nitrophenyl) methane, bis(4-hydroxy-2,6-dimethyl-3-methoxyphenyl) methane, 1,1-bis(4-hydroxyphenyl)ethane, 1,1-bis(4-hydroxy-2-chlorophenyl)ethane, 2,2-bis(4-hydroxyphenyl) propane (bisphenol A); 2,2-bis(3-chloro-4-hydroxyphenyl) propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5- isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-disopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 2,2-bis(4-hydroxy-3-ethylphenyl)propane, 2,2-bis(4-hydroxy-3,5-dimethylphenyl)propane, 2,2-bis(3,5,3',5'-tetrachloro-4,4'-dihydroxyphenyl)propane, bis(4-hydroxyphenyl) cyclohexylmethane, 2,2-bis(4-hydroxyphenyl)-1-phenylpropane, 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(4'-hydroxy-3'methylphenyl)cyclohexane (DMBPC), 1,1-bis(3,5-dimethyl-4-hydroxyphenyl)cyclohexane; 4,4'-[1-methyl-4-(1-methyl-ethyl)-1,3-cyclohexandiyl]bisphenol (1,3 BHPM), 4-[1-[3-(4-hydroxyphenyl)-4-methylcyclohexyl]-1-methyl-ethyl]-phenol (2,8 BHPM), 3,8-dihydroxy-5a,10b-diphenylcoumarano-2',3',2,3-coumarane (DCBP), 2-phenyl-3,3-bis(4-hydroxyphenyl)phthalimidine, 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; 1,1-bis(3-chloro-5-phenyl-4-hydroxyphenyl)cyclohexane; 1,1-bis(3-bromo-5-phenyl-4-hydroxyphenyl)cyclohexane; 1,1-bis(3,5-disopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4-hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6-dibromo-3,5-dimethyl-4-hydroxyphenyl) cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-disopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4-bis(4-hydroxyphenyl)heptane, 4,4'dihydroxy-1,1-biphenyl; 4,4'-dihydroxy-3,3'-dimethyl-1,1-biphenyl; 4,4'-dihydroxy-3,3'-dioctyl-1,1-biphenyl; 4,4'-(3,3,5-trimethylcyclohexylidene)diphenol, 4,4'-bis(3,5-dimethyl)diphenol, 4,4'-dihydroxydiphenylether; 4,4'-dihydroxydiphenylthioether; 1,3-bis(2-(4-hydroxyphenyl)-2-propyl)benzene; 1,3-bis(2-(4-hydroxy-3-methylphenyl)-2-propyl)benzene; 1,4-bis(2-(4-hydroxyphenyl)-2-propyl)benzene, 1,4-bis(2-(4-hydroxy-3-methylphenyl)-2-propyl)benzene 2,4'-dihydroxyphenyl sulfone, 4,4'-dihydroxydiphenylsulfone (BPS), bis(4-hydroxyphenyl) methane, 2,6-dihydroxy naphthalene; hydroquinone; resorcinol, C1-3 alkyl-substituted resorcinols, 3-(4-hydroxyphenyl)-1,1,3-trimethylindan-5-ol, 1-(4-hydroxyphenyl)-1,3,3-trimethylindan-5-ol, and 2,2,2',2'-tetrahydro-3,3,3',3'-tetramethyl-1,1'-spirobi[1H-indene]-6,6'-diol. The most typical aromatic dihydroxy compound is bisphenol A (BPA).

In some embodiments, a rigid aliphatic or a cycloaliphatic diol can be used as a comonomer with the AHP monomer to produce polycarbonate copolymers. Examples of rigid diols include isosorbide (also referred to as 1,4:3,6-dianhydro-D-glucitol), bis(hydroxymethyl)tricyclododecane, and the like, that tend to produce copolymers having higher glass transition temperatures, as compared to comonomer compositions which do not include these types of rigid aliphatic diols.

The carbonic acid diester described above has the general formula (XI),

wherein each Z is independently an aliphatic radical or an aromatic radical. Suitable examples of carbonic acid diesters include, but are not intended to be limited to, ditolyl carbonate, m-cresyl carbonate, dinaphthyl carbonate, diphenyl carbonate, diethyl carbonate, dimethyl carbonate, dibutyl carbonate, dicyclohexyl carbonate, and combinations of two or more carbonic acid diesters thereof. Diphenyl carbonate is widely used as a carbonic acid diester due to its low cost and ready availability on a commercial scale. If two or more of the carbonic acid diesters listed above are utilized, preferably one of the carbonic acid diesters is diphenyl carbonate.

Suitable carbonic acid diesters include the group of "activated aromatic carbonates". As used herein, the term "activated aromatic carbonate" is defined as a diaryl carbonate that is more reactive than diphenyl carbonate in a transesterification reaction. Such activated aromatic carbonates can also be represented by formula (XI), wherein each Z is an aryl radical having 6 to 30 carbon atoms. More specifically, the activated carbonates have the general formula (XII),

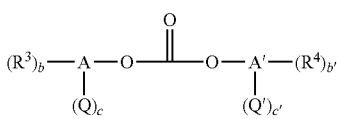

(XII)

wherein Q and Q' are each independently an ortho-positioned activating group; A and A' are each independently aromatic rings which can be the same or different depending on the number and location of their substituent groups, and c and c' is zero to a whole number up to a maximum equivalent to the number of replaceable hydrogen groups substituted on the aromatic rings A and A' respectively, provided c+c' is greater than or equal to 1. $R^3$ and $R^4$ are each independently substituent groups such as alkyl, substituted alkyl, cycloalkyl, alkoxy, aryl, alkylaryl, cyano, nitro, or halogen. The term b is zero to a whole number up to a maximum equivalent to the number of replaceable hydrogen atoms on the aromatic ring A minus the number c, and the number b' is zero to a whole number up to a maximum equivalent to the number of replaceable hydrogen atoms on the aromatic ring A' minus the number c'. The number, type and location of $R^3$ or $R^4$ on the aromatic ring is not intended to be limited unless they deactivate the carbonate and lead to a carbonate that is less reactive than diphenyl carbonate.

Non-limiting examples of suitable ortho-positioned activating groups Q and Q' include (alkoxycarbonyl)aryl groups, halogens, nitro groups, amide groups, sulfone groups, sulfoxide groups, or imine groups with structures indicated below,

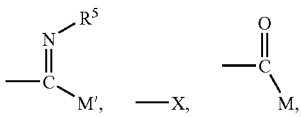

wherein X is halogen or $NO_2$; M and M' independently comprises N-dialkyl, N-alkyl aryl, alkyl, or aryl; and $R^5$ is alkyl or aryl.

Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl)carbonate, bis(o-formylphenyl)carbonate. Unsymmetrical combinations of these structures, wherein the substitution number and type on A and A' are different, are also contemplated. A preferred structure for the activated aromatic carbonate is an ester-substituted diaryl carbonate having the formula (XIII),

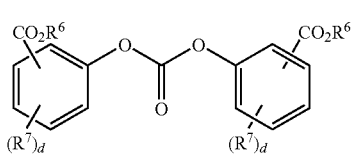

(XIII)

wherein $R^6$ is independently at each occurrence a $C_1$-$C_{20}$ alkyl radical, $C_4$-$C_{20}$ cycloalkyl radical, or $C_4$-$C_{20}$ aromatic radical; $R^7$ is independently at each occurrence a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and d is independently at each occurrence an integer from 0 to 4. At least one of the substituents $CO_2R^6$ is preferably attached in the ortho position of formula (XIII).

Examples of preferred ester-substituted diaryl carbonates include, but are not limited to, bis(methylsalicyl)carbonate (CAS Registry No. 82091-12-1) (also known as BMSC or bis(o-methoxycarbonylphenyl)carbonate), bis(ethyl salicyl) carbonate, bis(propyl salicyl) carbonate, bis(butylsalicyl) carbonate, bis(benzyl salicyl)carbonate, bis(methyl 4-chlorosalicyl)carbonate and the like. Preferably, BSMC is used in melt polycarbonate synthesis due to its lower molecular weight and higher vapor pressure.

Some non-limiting examples of non-activating groups which, when present in an ortho position, would not be expected to result in activated carbonates are alkyl, cycloalkyl or cyano groups. Some specific and non-limiting examples of non-activated carbonates include bis(o-methylphenyl)carbonate, bis(p-cumylphenyl)carbonate, bis(p-(1,1,3,3-tetramethyl)butylphenyl)carbonate and bis(o-cyanophenyl)carbonate. Unsymmetrical combinations of these structures are also expected to result in non-activated carbonates.

As used herein the term "activated carbonate" refers to a diaryl carbonate which is typically more reactive (either kinetically or thermodynamically) toward aromatic dihydroxy compounds than diphenyl carbonate under identical conditions. Activated carbonates are typically (but not necessarily) substituted diaryl carbonates. As used herein the term "structural units indicative of the activated carbonate" means either internal "kinks" in the copolycarbonate or end groups caused by incorporation of a fragment of an activated carbonate such as bis(methylsalicyl) carbonate (sometimes hereinafter referred to as "BMSC").

Unsymmetrical diaryl carbonates, wherein one aryl group is activated and one aryl is inactivated, are useful if the activating group renders the diaryl carbonate more reactive than diphenyl carbonate.

One method for determining whether a certain diaryl carbonate is activated or is not activated is to carry out a model melt transesterification reaction between the particular diaryl carbonate and a phenol such as para-(1,1,3,3-tetramethyl) butyl phenol (and comparing the relative reactivity against diphenyl carbonate). This phenol is preferred because it possesses only one reactive site, possesses a low volatility, and possesses a similar reactivity to bisphenol A. The model melt transesterification reaction is carried out at temperatures above the melting points of the particular diaryl carbonate and phenol in the presence of a transesterification catalyst, which is usually an aqueous solution of sodium hydroxide or sodium phenoxide. Preferred concentrations of the transesterification catalyst are at about 0.001 mole percent based on the number of moles of the phenol or diaryl carbonate. Although a preferred reaction temperature is 200° C., the choice of reaction conditions as well as catalyst concentration can be adjusted depending on the reactivity and melting points of the reactants to provide a convenient reaction rate. The reaction temperature is preferably maintained below the degradation temperature of the reactants. Sealed tubes can be used if the reaction temperatures cause the reactants to volatilize and affect the reactant molar balance. A determination of an equilibrium concentration of the reactants is accomplished through reaction sampling during the course of the reaction with subsequent analysis of the reaction mixture using well-known detection methods such as HPLC (high pressure liquid chromatography). Particular care needs to be taken so that the reaction does not continue after the sample has been removed from the reaction vessel. This is accomplished by cooling down the sample in an ice bath and by employing a reaction quenching acid, such as acetic acid in the water phase of the HPLC solvent system. It may also be desirable to introduce the reaction quenching acid directly into the reaction sample in addition to cooling the reaction mixture. A preferred concentration for the reaction quenching acid, e.g., acetic acid in the water phase of the HPLC solvent system, is about 0.05 mole percent. The equilibrium constant is then determined from the concentration of the reactants and product after equilibrium is reached. Equilibrium is assumed to have been reached when the concentration of components in the reaction mixture reach a point of little or no change on sampling of the reaction mixture. The equilibrium constant can be determined from the concentration of the reactants and products by methods well known to those skilled in the art. A diaryl carbonate which possesses a relative equilibrium constant ($K_{diarylcarbonate}/K_{diphenylcarbonate}$) of greater than 1 is considered to possess a greater reactivity than diphenyl carbonate and is a suitable activated aromatic carbonate for use in the present disclosure, whereas a diaryl carbonate which possesses an equilibrium constant of 1 or less is considered to possess the same or have less reactivity than diphenyl carbonate and is considered not to be activated. It is generally preferred to employ an activated aromatic carbonate with very high reactivity compared to diphenyl carbonate when conducting transesterification reactions. Preferred are activated aromatic carbonates with an equilibrium constant greater than at least 1,000 times that of diphenyl carbonate.

Polycarbonate compositions comprising the structural unit of formula (X) and carbonate units derived from the activated carbonate (XII) preferably comprise at least one end group derived from the activated carbonate. In one embodiment, the end groups which are indicative of the activated aromatic carbonate has a structure of formula (XIV),

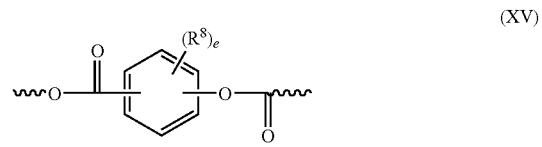

(XIV)

wherein Q is an ortho-positioned activating group; A is an aromatic ring, c is a whole number of 1 to the number of replaceable hydrogen groups substituted on the aromatic ring A; $R^3$ is a substituent group selected from the group consisting of alkyl, cycloalkyl, alkoxy, aryl, cyano, nitro, and halogen; and b is zero to a whole number to the number of replaceable hydrogen groups on the aromatic ring minus c. Q is preferably a radical independently selected from the group consisting of (alkoxycarbonyl)aryl groups, halogens, nitro groups, amide groups, sulfone groups, sulfoxide groups, or imine groups with structures:

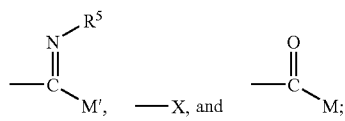

wherein X comprises halogen or $NO_2$, M and M' independently comprises N-alkyl, N-aryl, or N-alkyl aryl; $R^5$ comprises alkyl or aryl when c is 1; and c has a value of 0 or 1.

Polycarbonates prepared using ester-substituted diaryl carbonates, such as for example BMSC, may further comprise very low levels of structural features, which arise from side reactions taking place during the melt polymerization reaction between an ester-substituted diaryl carbonate of structure (XIII) and dihydroxy aromatic compounds of structure (X). One such structural feature has a structure of formula (XV),

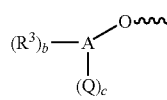

(XV)

wherein $R^8$ is a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and e is a whole number of 1-4. Typically structures of type (XV) are present only to a minor extent (e.g., 0.2 to 1 mole percent).

Structure (XV) is termed an internal ester-carbonate linkage or kink. Without wishing to be bound by any theory, it is thought that structure (XV) may arise by reaction of an ester-substituted phenol by-product, for example methyl salicylate, at its ester carbonyl group with a dihydroxy aromatic compound or a hydroxyl group of a growing polymer chain. Further reaction of the ester-substituted phenolic hydroxy group leads to formation of a carbonate linkage. Thus, the ester-substituted phenol by-product of reaction of an ester-substituted diaryl carbonate with a dihydroxy aromatic compound may be incorporated into the main chain of a linear polycarbonate, for example.

Another structural feature present in melt transesterification polymerization reactions between ester-substituted diaryl carbonates and dihydroxy aromatic compounds is the ester-linked terminal end group having a free hydroxyl group and have the structure (XVI),

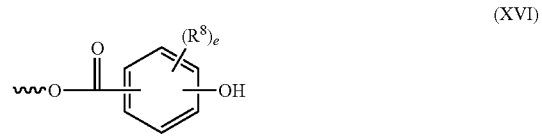

(XVI)

wherein $R^8$ and e are as defined above. Without wishing to be bound by any theory, it is believed that structure (XVI) may arise in the same manner as structure (XV), but without further reaction of the ester-substituted phenolic hydroxy group. In the structures provided herein, the wavy line represents the polycarbonate polymer chain structure. End capping of the polymer chains made by this method may be only partial. In typical embodiments of polycarbonates prepared by the methods described herein, the free hydroxyl group content is from 7 percent to 100 percent. This number may be varied by changing reaction conditions or by adding additional end-capping agents. In one embodiment, wherein the activated carbonate used is BMSC, there will be an ester linked end group of structure (XVII),

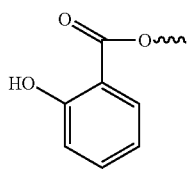
(XVII)

which possesses a free hydroxyl group. Thus, for example, if the terminal group of structure (XVII) is attached to a para, para-PPPBP unit in the polycarbonate chain then it is designated hereinafter as "p,p-PPPBP-salicyl-OH end", and if the terminal group of structure (XVII) is attached to a BPA unit in the polycarbonate chain, it is hereinafter designated as "BPA-salicyl-OH end".

The polycarbonates comprise structural units indicative of the activated carbonate. These structural units may be end groups produced when activated carbonate fragments act as end capping agents or may be kinks introduced into the copolymer by incorporation of activated carbonate fragments. In one embodiment the terminal end group is a methyl salicyl group of structure (XVIII).

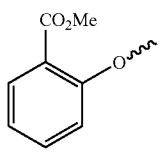
(XVIII)

It could also include other salicyl groups such as the ethylsalicyl, isopropylsalicyl, and butylsalicyl groups.

The method to be used for preparing polymers comprising structural units derived from the pure AHP and the ultra-pure AHP depends upon the type of polymer to be produced, and reactivity of the other monomers and/or other comonomers used. A number of polymerization methods can be used for producing a polymer, such as a homopolycarbonate or a copolycarbonate. Suitable methods for producing polycarbonates, for example, include a melt transesterification polymerization method, an interfacial polymerization method, and a bischloroformate polymerization method.

The melt transesterification polymerization method is generally carried out by combining a catalyst and a reactant composition to form a reaction mixture; and mixing the reaction mixture under reactive conditions for a time period effective to produce a polycarbonate product, wherein the reactant composition generally comprises a carbonic acid diester of the formula $(ZO)_2C=O$, wherein each Z is independently an unsubstituted or a substituted alkyl radical, or an unsubstituted or a substituted aryl radical and the pure and/or the ultra-pure AHP, such as for example, para, para-PPPBP.

During the manufacture of the polycarbonates by the melt transesterification method using the activated or unactivated carbonic acid diester, the amount of the carbonic acid diester comprises about 0.8 moles to about 1.30 moles, and more specifically about 0.9 moles to about 1.2 moles, based on one mole of the AHP or any combination of the AHP and at least one aromatic dihydroxy comonomer.

Suitable melt transesterification catalysts include alkali metal compounds, alkaline earth metal compounds, tetraorganoammonium compounds, and tetraorganophosphonium compounds, combinations comprising at least one of the foregoing catalysts.

Specific examples of alkali metal compounds or alkaline earth metal compounds include organic acid salts, inorganic acid salts, oxides, hydroxides, hydrides, and alcoholates of alkali metals and alkaline earth metals. In an embodiment, the catalyst is an alkali metal compound of the formula $M_1X_1$, wherein $M_1$ is selected from the group consisting of lithium, sodium, and potassium; and $X_1$ is selected from the group consisting of hydroxide and OAr, wherein Ar is a monovalent aromatic radical.

More specifically, examples of suitable alkali metal compounds include, but are not limited to, sodium hydroxide, potassium hydroxide, lithium hydroxide, calcium hydroxide, magnesium hydroxide, sodium bicarbonate, potassium bicarbonate, lithium bicarbonate, sodium carbonate, potassium carbonate, lithium carbonate, sodium acetate, potassium acetate, lithium acetate, lithium stearate, sodium stearate, potassium stearate, lithium hydroxyborate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts, dipotassium salts, and dilithium salts of bisphenol A, and sodium salts, potassium salts, lithium salts of phenol, and the like.

Specific examples of alkaline earth metal compounds include, but are not limited to, calcium hydroxide, barium hydroxide, magnesium hydroxide, strontium hydroxide, calcium bicarbonate, barium bicarbonate, magnesium bicarbonate, strontium bicarbonate, calcium carbonate, barium carbonate, magnesium carbonate, strontium carbonate, calcium acetate, barium acetate, magnesium acetate, strontium acetate, strontium stearate, and the like.

Exemplary tetraorganoammonium compounds include compounds comprising structure (XIX),

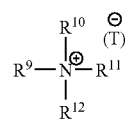
(XIX)

wherein $R^9$ to $R^{12}$ are each independently a $C_1$-$C_{20}$ alkyl radical, $C_4$-$C_{20}$ cycloalkyl radical or a $C_4$-$C_{20}$ aryl radical and $(T)^-$ is an organic or an inorganic anion. Suitable anions $(T)^-$ include hydroxide, halide, carboxylate, sulfonate, sulfate, carbonate and bicarbonate. In one embodiment, the transesterification catalyst comprises tetramethyl ammonium hydroxide.

In still other embodiments, the catalyst is a tetraorganophosphonium compound. Exemplary quaternary phosphonium compounds include compounds comprising structure (XX),

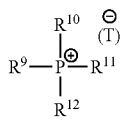

(XX)

wherein $R^9$ to $R^{12}$ and $(T)^-$ are as previously described.

Illustrative anions include hydroxide, halide, carboxylate, sulfonate, sulfate, carbonate, and bicarbonate. Where $(T)^-$ is a polyvalent anion such as carbonate or sulfate it is understood that the positive and negative charges in structures (XIX) and (XX) are properly balanced. For example, when $R^9$ to $R^{12}$ in structure (XIX) are each methyl groups and $(T)^-$ is carbonate, it is understood that $(T)^-$ represents $\frac{1}{2}(CO_3^{-2})$ as will be appreciated by those skilled in the art.

Specific examples of tetraorganoammonium compounds and tetraorganophosphonium compounds include, but are not limited to tetramethylammonium hydroxide, tetrabutylammonium hydroxide, tetraethylphosphonium hydroxide, tetrabutylphosphonium acetate, tetrabutylphosphonium hydroxide, and the like. In one embodiment, the catalyst comprises tetrabutyl phosphonium acetate. In an alternate embodiment, the catalyst comprises a mixture of an alkali metal salt or alkaline earth metal salt with at least one quaternary ammonium compound, at least one quaternary phosphonium compound, or a mixture thereof. For example, the catalyst may be a mixture of sodium hydroxide and tetrabutylphosphonium acetate. In another embodiment, the catalyst is a mixture of sodium hydroxide and tetramethyl ammonium hydroxide. In another embodiment, the catalyst comprises an alkaline earth metal salt of an organic acid, an alkali metal salt of an organic acid, or a salt of an organic acid comprising both alkaline earth metal ions and alkali metal ions. Alkali metal and alkaline earth metal salts of organic acids, such as for example, formic acid, acetic acid, stearic acid and ethylenediamine tetraacetic acid can also be used. In one embodiment, the catalyst comprises magnesium disodium ethylenediamine tetraacetate (EDTA magnesium disodium salt). In yet another embodiment, the catalyst comprises the salt of a non-volatile inorganic acid. By "non-volatile" it is meant that the referenced compounds have no appreciable vapor pressure at ambient temperature and pressure. In particular, these compounds are not volatile at temperatures at which melt polymerizations of polycarbonate are typically conducted. The salts of non-volatile acids are alkali metal salts of phosphites; alkaline earth metal salts of phosphites; alkali metal salts of phosphates; and alkaline earth metal salts of phosphates. Suitable salts of non-volatile acids include $NaH_2PO_3$, $NaH_2PO_4$, $Na_2H_2PO_3$, $KH_2PO_4$, $CsH_2PO_4$, $Cs_2H_2PO_4$, or a mixture thereof. In one embodiment, the transesterification catalyst comprises both the salt of a non-volatile acid and a basic co-catalyst such as an alkali metal hydroxide. This concept is exemplified by the use of a combination of $NaH_2PO_4$ and sodium hydroxide as the transesterification catalyst.

Any of the catalysts disclosed above may be used as combinations of two or more substances. The catalyst may be added in a variety of forms. The catalyst may be added as a solid, for example as a powder, or it may be dissolved in a solvent, for example, in water or alcohol. The total catalyst composition is preferably about $1 \times 10^{-7}$ to about $2 \times 10^{-3}$ moles, and with about $1 \times 10^{-6}$ to about $4 \times 10^{-4}$ moles more preferred for each mole of the combination of the pure AHP (and/or ultra-pure AHP) and the aromatic dihydroxy compound comonomer.

Any of the catalysts described above for use in polycarbonate melt transesterification reactions may be used in reactions involving activated carbonates. It is often advantageous to use a combination of some amount of a salt of an alkaline earth metal and/or an alkali metal (i.e., an "alpha" catalyst) that does not degrade at temperatures used throughout the reaction together with a quaternary ammonium and/or a quaternary phosphonium compound that does degrade at a temperature used in the reaction (i.e., a "beta" catalyst). The total amount of catalyst employed is about $1 \times 10^{-7}$ to about $1 \times 10^{-2}$, and preferably about $1 \times 10^{-7}$ to about $2 \times 10^{-3}$ moles catalyst per total moles of the mixture of the AHP and any aromatic dihydroxy compound comonomer employed.

The reactants for the polymerization reaction using an activated aromatic carbonate can be charged into a reactor either in the solid form or in the molten form. Initial charging of reactants into a reactor and subsequent mixing of these materials under reactive conditions for polymerization may be conducted in an inert gas atmosphere such as a nitrogen atmosphere. The charging of one or more reactant may also be done at a later stage of the polymerization reaction. Mixing of the reaction mixture is accomplished by any methods known in the art, such as by stirring. Reactive conditions include time, temperature, pressure and other factors that affect polymerization of the reactants. Typically, the activated aromatic carbonate is added at a mole ratio of about 0.8 to about 1.3, and more specifically, 0.9 to about 1.2 and all sub-ranges there between, relative to the total moles of aromatic dihydroxy compound and aliphatic diol.

The melt polymerization reaction using the activated aromatic carbonate is conducted by subjecting the above reaction mixture to a series of temperature-pressure-time protocols. In some embodiments, this involves gradually raising the reaction temperature in stages while gradually lowering the pressure in stages. In one embodiment, the pressure is reduced from about atmospheric pressure at the start of the reaction to about 0.01 millibar (1 Pascal) or in another embodiment to 0.05 millibar (5 Pascals) in several steps as the reaction approaches completion. The temperature may be varied in a stepwise fashion beginning at a temperature of about the melting temperature of the reaction mixture and subsequently increased to about 320° C. In one embodiment, the reaction mixture is heated from about ambient (about 21 to 23° C.) temperature to about 150° C. The polymerization reaction starts at a temperature of about 150° C. to about 220° C., then is increased to about 220° C. to about 250° C. and is then further increased to a temperature of about 250° C. to about 320° C. and all sub-ranges there-between. The total reaction time is about 30 minutes to 200 minutes and all sub-ranges there-between. This procedure will generally ensure that the reactants react to give polycarbonates with the desired molecular weight, glass transition temperature and physical properties. The reaction proceeds to build the polycarbonate chain with production of a by-product such as, for example an ester-substituted alcohol e.g., methyl salicylate. Efficient removal of the by-product may be achieved by different techniques such as reducing the pressure. Generally the pressure starts relatively high in the beginning of the reaction, such as atmospheric pressure in one embodiment, and is lowered progressively throughout the reaction and temperature is raised throughout the reaction. Experimentation is needed to find the most efficient conditions for particular production equipment.

The progress of the reaction may be monitored by measuring the melt viscosity or the weight average molecular weight of the reaction mixture using techniques known in the art such as gel permeation chromatography. These properties may be measured by taking discreet samples or may be measured on-line. After the desired melt viscosity and/or molecular weight is reached, the final polycarbonate product may be isolated from the reactor in a solid or molten form. It will be appreciated by a person skilled in the art that the polycarbonates as described in the preceding sections may be made in a batch or a continuous process and the process disclosed herein is desirably carried out in a solvent free mode. Reactors chosen should ideally be self-cleaning and should minimize any "hot spots."

The polycarbonates may also be prepared in an extruder in the presence of one or more catalysts, wherein the carbonic acid diester is an activated aromatic carbonate. The reactants for the polymerization reaction can be fed to the extruder in powder or molten form. In one embodiment, the reactants are dry blended prior to addition to the extruder. The extruder may be equipped with pressure reducing devices (e.g., vents), which serve to remove the activated phenol by-product and thus drive the polymerization reaction toward completion. The molecular weight of the polycarbonate product may be manipulated by controlling, among other factors, the feed rate of the reactants, the type of extruder, the extruder screw design and configuration, the residence time in the extruder, the reaction temperature and the pressure reducing techniques present on the extruder. The molecular weight of the polycarbonate product may also depend upon the structures of the reactants, such as the AHP, the activated aromatic carbonate, the dihydroxy aromatic compound comonomer (if used), and the catalyst employed. Many different screw designs and extruder configurations are commercially available that use single screws, double screws, vents, back flight and forward flight zones, seals, side-streams and sizes. One skilled in the art may have to experiment to find the best designs using generally known principals of commercial extruder design.

The process disclosed herein can be used to prepare AHP polycarbonates. Thus polycarbonate homopolycarbonate and copolycarbonates comprising structural units derived from para, para-PPPBP having a weight average molecular weight ($M_w$) of about 3,000 to about 150,000 and a glass transition temperature ($T_g$) of about 80° C. to about 300° C. can be prepared. The number average molecular weights ($M_n$) of the homopolycarbonate and copolycarbonates can be from about 1,500 to about 75,000.

In monitoring and evaluating polycarbonate synthesis, it is of particular interest to determine the concentration of Fries product present in the polycarbonate. The generation of significant Fries product can lead to polymer branching, resulting in uncontrollable melt behavior. In the process of preparing polycarbonates described herein, some branching reaction (Fries reaction) takes place (especially at higher temperatures and exacerbated by alpha catalysts) resulting in a Fries product. Fries products are defined as structural units of the product polycarbonate which upon hydrolysis of the product polycarbonate afford a carboxy-substituted dihydroxy aromatic compound bearing a carboxy group adjacent to one or both of the hydroxy groups of the carboxy-substituted dihydroxy aromatic compound. For example, in bisphenol A polycarbonate prepared by a melt polymerization method in which Fries reaction occurs, the Fries product comprises structure (XXI):

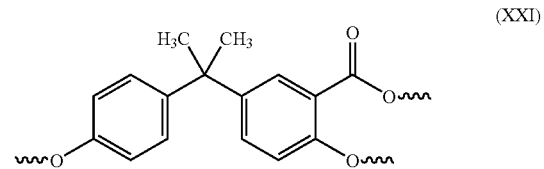

(XXI)

that upon complete hydrolysis of the product polycarbonate affords 2-carboxy bisphenol A. As indicated, the Fries product may serve as a site for polymer branching, the wavy lines of structure (XXI) indicating a polymer chain structure.

The polycarbonates prepared using the activated carbonate by the disclosed method have a concentration of Fries product of less than 500 parts per million (ppm) as measured by high performance liquid chromatography (HPLC). The Fries concentration is much less than what is obtained in a conventional melt polymerization process that uses diphenyl carbonate as the carbonic acid diester. Fries products are generally undesirable for certain polycarbonates because excessive levels can adversely affect certain physical properties.

In the interfacial polymerization method, the AHP monomer, with or without one or more comonomers (such as an aliphatic diol, or a aromatic dihydroxy compound), and phosgene are reacted in the presence of an acid acceptor and an aqueous base to produce the polycarbonate. Tertiary amines, such as for example, trialkylamines are preferably used as acid acceptors. An exemplary trialkylamine is triethylamine. Suitable aqueous bases include, for example, the alkali metal hydroxides, such as sodium hydroxide. The interfacial method can be used for producing polycarbonates comprising structural units derived from an AHP, and preferably having molecular weights greater than about 50,000, as measured using gel permeation chromatography (abbreviated as "GPC"), relative to polystyrene standards in dichloromethane as a solvent.

The interfacial method described above can be suitably adapted to produce polycarbonates through the intermediate formation of a 2-aryl-3,3-bis(4-hydroxyaryl)phthalimidine bischloroformate. This method is sometimes called the bischloroformate polymerization method. In one embodiment, the method comprises reacting an AHP with phosgene in an organic solvent, and then reacting the bischloroformate either with an AHP, or an aromatic dihydroxy compound in the presence of an acid acceptor and an aqueous base to form the polycarbonate.

The interfacial polymerization method and the bischloroformate polymerization method can be carried in a batch or a continuous mode using one or more reactor systems. To carry out the process in a continuous mode, one or more continuous reactors, such as for example, a tubular reactor can be used. In one embodiment, the continuous method comprises introducing into a tubular reactor system phosgene, at least one solvent (example, methylene chloride), at least one bisphenol, aqueous base, and optionally one or more catalysts (example, a trialkylamine) to form a flowing reaction mixture. The flowing mixture is then passed through the tubular reactor system until substantially all of the phosgene has been consumed. The resulting mixture is next treated with a mixture comprising an aqueous base, at least one end-capping agent, optionally one or more solvents, and at least one catalyst. The end-capped polycarbonate thus formed is continuously removed from the tubular reactor system. The process can be used for preparing end-capped polycarbonate oligomers (generally polycarbonates having a weight average molecular weight of less than 10,000 daltons) or polymers having a weight average molecular weight of greater than 10,000 daltons. The processes outlined hereinabove can also be suitably adapted, for example, to produce end-capped polycarbonates via the intermediate formation of a mixture comprising an AHP monochloroformate or an AHP bischloroformate.

In another embodiment, polymer blends comprise the polymers comprising structural units derived from the pure AHP and/or the ultra-pure AHP (described previously) and at least one thermoplastic polymer. The thermoplastic polymer is selected from the group consisting of vinyl polymers, acrylic polymers, polyacrylonitrile, polystyrenes, polyolefins, polyesters, polyurethanes, polyamides, polysulfones, polyimides, polyetherimides, polyphenylene ethers, polyphenylene sulfides, polyether ketones, polyether ether ketones, ABS resins, polyethersulfones, poly(alkenylaromatic) polymers, polybutadiene, polyacetals, polycarbonates, polyphenylene ethers, ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, tetrafluoroethylene, polycarbonate-polyorganosiloxane block copolymers, copolymers comprising aromatic ester, estercarbonate, and carbonate repeat units; mixtures, and blends comprising at least one of the foregoing polymers.

The polymers and polymer blends described hereinabove are valuable for producing articles. In one embodiment, an article comprises a polymer comprising structural units derived from an AHP, which comprises less than 200 ppm of an AHAP impurity, relative to an overall weight of the AHP. In another embodiment, an article comprises a polymer comprising structural units derived from an AHP, which comprises less than 200 ppm of an AHAP impurity and less than 500 ppb of metals impurity, relative to an overall weight of the AHP. In still another embodiment, an article comprises less than 200 ppm of an AHAP impurity and less than 500 ppb of metals impurity, relative to an overall weight of the AHP. The thus molded articles have a yellowness index of less than 20 in an embodiment, and less than 10 in another embodiment.

Polymers, particularly polycarbonate homopolymers and copolymers comprising structural units derived from the pure and the ultra-pure AHP have an APHA value of less than 20, as measured using ASTM E313-00 test method, published February 2001. Hence these polymers are useful for producing articles having a number of useful properties, such as a low residual color. The articles also exhibit excellent heat aging. The polycarbonates described herein have high glass transition temperatures of higher than or equal to about 180° C. One of the unique properties of these polycarbonates, especially those that have glass transition temperatures of greater than or equal to about 180° C. is that during melt processing they exhibit a shear-thinning behavior. That is, the polymers have the ability to flow under an applied shear. Therefore, standard melt processing equipment used for BPA polycarbonates can advantageously be used for producing articles. Moreover, articles having transparency and the other advantageous properties of a bisphenol A homopolymer polycarbonate, but with a significantly higher $T_g$ can be made from these polycarbonates. Lenses in applications where they are exposed to heat are a good example of such an application. Non-limiting examples of suitable articles that can be prepared include an automotive headlamp inner lens, an automotive headlamp outer lens, an automotive fog lamp lens, an automotive bezel, a medical device, a display device, electrical connectors, under the hood automotive parts, and projector lens. Examples of suitable display devices include a laptop computer screen, a liquid crystal display screen, and an organic light-emitting diode display screen.

The polycarbonates disclosed herein may also be combined with effective amounts of one or more of various types of additives used selected from the group consisting of fillers, fire retardants, drip retardants, antistatic agents, UV stabilizers, heat stabilizers, antioxidants, plasticizers, dyes, pigments, colorants, processing aids, and mixtures thereof. These additives are known in the art, as are their effective levels and methods of incorporation. Effective amounts of the additives vary widely, but they are usually present in an amount up to about 50% or more by weight, based on the weight of the entire composition. Especially desirable additives include hindered phenols, thio compounds and amides derived from various fatty acids. The desired amounts of these additives generally ranges up to about 2% total combined weight based on the total weight of the composition.

EXAMPLES

In the following examples, molecular weights were measured by gel permeation chromatography using a polystyrene standard. Glass transition temperatures of the polycarbonates were measured by differential scanning calorimetry by heating the sample at the rate of 10° C. to 20° C. per minute under nitrogen.

HPLC analysis was generally carried out by using an HPLC instrument equipped with a $C_{18}$ (reverse phase) column and a Photo Diode Array detector. A solvent mixture of methanol, water, and acetonitrile of varying relative proportions was used. Area percent assay was computed from the area value for each peak detected in the chromatogram divided by the total area from all peaks detected. To measure weight percent assay, calibration curves for para, para-PP-PBP, ortho, para-PPPBP, AP, and phenolphthalein were first generated. Then the weight percent of a given component in a sample was calculated using these calibration curves.

Yellowness index of polymer samples were measured in chloroform solutions using ASTM E 313-00 test method, published in February 2001. Yellowness index of the polymer sample was measured on a 10 weight percent (weight/volume) solution in chloroform using a Macbeth Instrument. The YI shift relative to blank (chloroform) is given as the YI for the polymer sample. Weight average and number average molecular weights were measured using GPC technique with a Shimadzu gel permeation chromatograph and using polystyrene standards. The polymer solution had a concentration of 1 milligram per milliliter.

Yellowness index (APHA) of the pure and ultra-pure AHP samples were measured as solutions in dimethyl sulfoxide using ASTM D1209 test method, published July 2000.

The acidity of the acidic ion exchange resin, expressed as milliequivalents of $H^+$ per gram of resin (meq/g), was determined by a method known in the art. The resin was treated with 20 weight percent aqueous sodium chloride solution, and the liberated hydrochloric acid was titrated against aqueous sodium hydroxide.

Example 1

Preparation of Para, Para-PPPBP

In a 500 milliliter four neck round bottom flask fitted with a overhead stirrer, a nitrogen gas inlet, thermo-well, and a condenser fitted with a Dean-Stark apparatus were placed 100 grams (0.3141 mole) of phenolphthalein, 117 grams (1.25 mole) of aniline, and 32.8 milliliters of 35% aqueous HCl (0.3141 mole). A slow stream of nitrogen gas was continuously passed through the flask, and the reaction mixture was heated at 100 to 120° C. for 2 to 3 hours to remove the water.

After approximately 21 milliliters of water had been collected, the hot reaction mixture was heated at 155 to 160° C. for 22 to 24 hours. Then the reaction mixture was cooled to 100 to 110° C., 250 milliliters of 10% aqueous HCl was poured into the reaction mass, and the resulting mixture was stirred for about 2 hours. The precipitate formed was filtered out, washed with water (5×100 milliliters) until the washings were free of acid, and dried to furnish crude PPPBP product. The crude material was dissolved in 700 milliliters of 4% aqueous sodium hydroxide solution, treated with 5 grams of activated charcoal, and stirred for about 1 hour. The solution was filtered, and the filtrate was acidified with 280 milliliters of 10% aqueous HCl to precipitate para, para-PPPBP, which was filtered and washed with free until the washings were neutral to pH, and dried to provide 117.5 grams (95% of theoretical yield) of para, para-PPPBP. HPLC analysis showed that the product contained 99.15 weight percent of para, para-PPPBP and 0.6 weight percent of AP impurity. The material had an APHA value of 126. This material was used as a feed for preparing the purified para, para-PPPBP and the ultra-pure para, para-PPPBP.

Examples 2 to 12 and Comparative Examples 1 to 3

General procedure to prepare purified para, para-PPPBP by removal of AP impurity from a para, para-PPPBP feed. The para, para-PPPBP prepared in Example 1 was used as the feed for the purification.

A sample of the para, para-PPPBP dissolved in a suitable solvent was treated with an acidic material. The ratio of the weight of the para, para-PPPBP to the weight of the acidic material taken was 1:1, respectively. With solid acidic materials, such as acidic ion exchange resins, the treatment was carried out either with columns packed with the acidic material, or they were stirred with the solution of the para, para-PPPBP. With other acidic materials such as organic acid chlorides and acid anhydrides, the process was conducted using a suitable organic solvent. On a volume/volume basis, para, para-PPPBP was found to be soluble in 50 volumes of methanol (A), 12 to 15 volumes of isopropanol (B), 20 volumes of 90:10 (volume/volume) of isopropanol/water (C), 15 volumes of 80:20 (volume/volume) isopropanol/water (D), 4 volumes of phenol, 4 volumes of 80:20 (volume/volume) of phenol/water (E), and 4 to 6 volumes of 90:10 (volume/volume) acetone/water (F). The purification process was carried out in a continuous process using a packed column of the acidic material, or in a batch process using any of the solid or the liquid acidic materials. The para, para-PPPBP feed material had 0.37 weight percent of AP as impurity. For each experiment in Table 1, the treatment with the acidic material was carried out for 1 to 2 hours. The para, para-PPPBP isolated after the treatment was then triturated with methanol to remove phenolphthalein to provide a purified para, para-PPPBP which was used for preparing polycarbonates using phosgene as the carbonate equivalent. The control-1 sample is the sample prepared in Example 1.

TABLE 1

| Example number | Acidic Material | Weight ratio of acidic material and para, para-PPPBP Feed | Solvent system | AP level (ppm) |
| --- | --- | --- | --- | --- |
| Control-1 | none | NA | NA | |
| 3 | Lewatit K1131 | 1:1 | A | 75 |
| 4 | Lewatit K1131 | 1:1 | B | <50 |
| 5$^a$ | Lewatit K1131 | 1:1 | C | <50 |
| 6 | Lewatit K1131 | 1:1 | D | <50 |
| 7 | Lewatit K1131 | 1:1 | E | <50 |
| 8 | Lewatit K1131 | 1:1 | F | <50 |
| 9 | T-63 | 1:2 | B | <50 |
| 10 | T-63 | 1:2 | C | <50 |
| 11 | DBSA | 1:10 | A | <50 |
| 12 | DBSA | 1:2 | A | <50 |
| 1* | A-121 | 1:1 | C | 1937 |
| 2* | A-15 | 1:1 | C | 1713 |
| 3* | A-21 | 1:1 | C | 1631 |

$^a$The APHA color value for the purified sample was 16.

The results from Table 1 show that acidic materials such as ion exchange resins and liquid acidic materials are effective in removing AP from a para, para-PPPBP feed having 0.6 weight percent or 6000 ppm of AP impurity to give a purified material having less than 50 ppm of the AP. Further, ion exchange resins crosslinked with 2% divinylbenzene (DVB) are more effective than IERs crosslinked with 20% DVB in removing AP impurity. Further, Comparative Examples 1 to 3 show that when the mole ratio of A-121 resin to the feed sample is changed to 1:1, the AP levels in the resulting AHP is much higher. Furthermore, Example 5 shows that the APHA color of purified para, para-PPPBP after treatment with the ion exchange resin followed by trituration with methanol results in a drastic reduction in the APHA color.

Examples 13 to 15

These Examples illustrate the general procedure for removing the AP impurity from a para, para-PPPBP feed by using phthalic anhydride as an organic anhydride.

A sample of impure para, para-PPPBP (5 grams) was treated with 30 milliliters of ortho-dichlorobenzene, treated with a calculated amount of phthalic anhydride, and refluxed for about 4 hours. Then the solution was cooled to ambient temperature, filtered, and washed with ortho-dichlorobenzene. Results are shown in

TABLE 2

| Example number | Organic anhydride | Weight ratio of organic anhydride to feed PPPBP | Solvent system | AP level (ppm) |
| --- | --- | --- | --- | --- |
| Control-2 | none | | none | 3142 |
| 13 | Phthalic anhydride | 1:0.06 | Ortho dichlorobenzene | 100 |
| 14 | Phthalic anhydride | 1:0.03 | Ortho dichlorobenzene | 120 |
| 15 | Phthalic anhydride | 1:0.006 | Ortho dichlorobenzene | 680 |

Table 3 shows that when the amount of phthalic anhydride relative to para, para-PPPBP feed is reduced, the AP impurity level increases.

Examples 16 to 18, and Comparative Example 4

These examples describe a general procedure for removing AP impurity from a para, para-PPPBP feed sample in a batch process using an acidic ion exchange resin.

The feed sample containing 0.6 weight percent of AP impurity was dissolved in a 90:10 (volume/volume) mixture of IPA and water, respectively. To this mixture was added an appropriate amount of Lewatit K1131 ion exchange resin, and the resulting mixture was shaken for 60 minutes, filtered, and the solvent was evaporated to give a solid residue, which was analyzed for AP content by HPLC. Results are shown in Table 3.

TABLE 3

| Example Number | Weight ratio of para, para-PPPBP feed to Lewatit K1131 | ppm of AP in purified PPPBP |
|---|---|---|
| 16 | 1:2 | 50 |
| 17 | 1:1 | 84 |
| 18 | 1:0.5 | 178 |
| 4* | 1:0.25 | 337 |

*Indicates Comparative Example

The results in Table 3 show that as the weight of the ion exchange resin relative to the feed sample is reduced, the AP impurity level in the resulting para, para-PPPBP increases, and at a weight ratio of 1:0.25, the AP level is greater than 200 ppm.

Examples 19 and 20, and Comparative Examples 5 and 6

These examples illustrate the effect of temperature on the ability of the acidic material to remove the AP impurity from a feed para, para-PPPBP material having 3570 ppm of AP as impurity. The process was studied by treating a solution of para, para-PPPBP feed in 20 volumes of 90:10 isopropanol/water, respectively with Lewatit K1131 ion exchange resin in a batch process at temperatures ranging from ambient to 70° C. Results are shown in Table 4, where the values represent ppm of AP in the treated para, para-PPPBP after the indicated time. "ND" stands for "not detected", which means the value is below the detection limit (less than 10 ppm) of the HPLC instrument. "NA" stands for "not applicable".

TABLE 4

| Treatment time (hours) | Example 19 Ambient Temperature | Example 20 50° C. | Comparative Example 5 60° C. | Comparative Example 6 70° C. |
|---|---|---|---|---|
| 0 | 3570 | 3570 | 3570 | 3570 |
| 1 | ND | ND | 30 | 301 |
| 2 | 24 | ND | 54 | 279 |
| 3 | 25 | 19 | 77 | 278 |
| 4 | 25 | 41 | 155 | 320 |
| 5 | NA | 44 | 125 | 357 |
| 6 | NA | 42 | 190 | NA |

Table 4 shows that as the temperature increases, the purification efficiency of the ion exchange resin decreases. Para, para-PPPBP having less than 50 ppm of AP can be obtained by operating at a temperature from ambient to about 50° C. Temperatures of about 40 to 50° C. are preferred to minimize the precipitation of adducts of para, para-PPPBP with solvents, such as isopropyl alcohol (IPA).

Example 21

This experiment illustrates that the acidic ion exchange resins can be regenerated and re-used efficiently at least 7 times over without any significant loss of activity to prepare para, para-PPPBP having less than 200 ppm of AP. The solvent used was a 80:20 mixture of acetone and water, respectively. The sample was heated to 40° C. and introduced into a column packed with Lewatit K 1131 IER at a weighted hourly space velocity of 7. Results are shown in Table 5. In the $3^{rd}$ recycle, the dilution of para, para-PPPBP feed was done with 12 volumes of the solvent instead of 6 volumes of solvent.

TABLE 5

| | Run Time (h) | PPPBP quantity (grams) | ppm AP in effluent |
|---|---|---|---|
| $1^{st}$ Cycle | 0 | 0 | 0 |
| | 12 | 60 | 18 |
| | 21 | 45 | 75 |
| | 26 | 25 | 105 |
| $1^{st}$ recycle after $1^{st}$ regeneration with con. HCl | 0 | 0 | 0 |
| | 1 | 5 | 51 |
| | 5 | 20 | 41 |
| | 13 | 40 | 45 |
| | 17 | 20 | 56 |
| | 29 | 60 | 85 |
| | 31 | 10 | 139 |
| $2^{nd}$ recycle after $2^{nd}$ regeneration with con. HCl | 0 | 0 | 0 |
| | 1 | 5 | 0 |
| | 3 | 10 | 0 |
| | 7 | 20 | 11 |
| | 10 | 15 | 40 |
| | 17 | 35 | 100 |
| | 23 | 30 | 156 |
| $3^{rd}$ recycle after $3^{rd}$ regeneration with con. HCl | 0 | 0 | 0 |
| | 2 | 10 | 9 |
| | 3 | 5 | 10 |
| | 6 | 15 | 12 |
| | 9 | 15 | 10 |
| | 10 | 5 | 17 |
| | 14 | 20 | 15 |
| | 19 | 25 | 19 |
| | 21 | 10 | 23 |
| $4^{th}$ recycle after $4^{th}$ regeneration with con. HCl | 0 | 0 | 0 |
| | 5 | 25 | 11 |
| | 8 | 15 | 14 |
| | 12 | 20 | 17 |
| | 15 | 15 | 19 |
| | 18 | 15 | 18 |
| | 20 | 10 | 21 |
| $5^{th}$ recycle after $5^{th}$ regeneration with con. HCl | 0 | 0 | 0 |
| | 10 | 50 | 0 |
| | 15 | 25 | 0 |
| | 17 | 10 | 13 |
| | 20 | 15 | 16 |
| $6^{th}$ recycle after $6^{th}$ regeneration with con. HCl | 0 | 0 | 0 |
| | 4 | 20 | 85 |
| | 20 | 80 | 105 |
| $7^{th}$ recycle after $7^{th}$ regeneration with con. HCl | 0 | 0 | 0 |
| | 16 | 80 | 10 |
| | 20 | 20 | 12 |

Spent ion exchange resin having a reduced acidity value was regenerated using the following representative procedure. The ion exchange resin (2 grams) having an acidity of 3.47 meq/g was shaken with a mixture of 16 milliliters of acetone, 4 milliliters of water, and 5 milliliters of concentrated hydrochloric acid for 3 to 4 hours. The resulting mixture, which contained a greenish-yellow solution, was filtered, washed with aqueous acetone, then washed with 100 milliliters of water until the washings were neutral to pH, and dried under vacuum to provide a regenerated ion exchange resin having an acidity of 4.54 meq/g (Fresh ion exchange resin had an acidity value of 4.88 meq/g). The procedure can also be used to regenerate spent ion exchange resin resulting from a process wherein a packed bed of the resin is used to remove AP impurity from a para, para-PPPBP feed.

Example 22

General procedure for a batch process for removing metal impurities from a para, para-PPPBP feed to prepare ultra-pure para, para-PPPBP.

Into a 1 liter Schott Duran bottle equipped with a cap was charged 13 volumes of a 90:10 volume ratio of isopropanol (IPA) and water for each gram of para, para-PPPBP feed. The contents of the bottle were heated on a water bath maintained at 65° C. till the PPPBP solid dissolved completely. 20 weight percent of the metal oxide adsorbent (relative to the weight of the PPPBP feed) was added and shaken at 20 revolutions per minute (RPM) for about 5 hours at ambient temperature. The metal oxide was filtered on a Buchner funnel and washed with 40 milliliters of IPA. The filtrate was then concentrated on a rotary evaporator at 70° C., initially at a pressure of about 300 millibars, and then at 175 millibars to furnish a slurry, which contained the para, para-PPPBP/IPA adduct as a precipitate. The slurry was filtered using 50 milliliters of Millipore water, suction dried to dryness, and transferred to the 1 liter Schott Duran bottle. To this was added 400 milliliters of Millipore water, and the mixture was heated to 85° C. in a water bath for about 1.5 hours. The hot mixture was then filtered on a Buchner funnel, washed with 200 milliliters of hot water maintained at a temperature of about 85° C., suction dried, and then dried overnight in a vacuum oven maintained at 125° C. The final para, para-PPPBP thus obtained in a recovery of greater than 95 weight percent was measured for color and purity. Metals assay in the product was determined using the ICP instrument.

Examples 23 to 28

The procedure described in Example 22 was used to remove metals and improve color from either a para, para-PPPBP feed that is used for preparing a pure para, para-PPPBP, or a pure para, para-PPPBP feed for preparing an ultra-pure para, para-PPPBP The procedure was repeated for other adsorbent candidates using other solvent systems. The data is shown in Table 6. Control-3 represents a pure para, para-PPPBP having less than 200 ppm of AP, which was obtained by treatment of the para, para-PPPBP of Example 1 with an ion exchange resin to remove AP impurity, followed by trituration with methanol to remove phenolphthalein. E-23 to E-28 represent Examples 23 to 28, respectively. The modified silica in Example 27 was prepared by boiling silica adsorbent with demineralized water for about 1 hour, filtering and drying under vacuum at about 120° C.

Examples 29, 30, and Comparative Example 7

General procedure for preparing a polycarbonate copolymer from a purified or an ultra-pure para-PPPBP prepared as described above.

The polymerization runs were carried out using a monomer mixture comprising 55 mole percent of bisphenol A (BPA) and 45 mole percent of para, para-PPPBP using bis(methyl) salicyl carbonate (BMSC). A glass polymerization reactor was passivated by soaking the reactor in a bath containing 1 molar aqueous hydrochloric acid solution. After 24 hours, the reactor was thoroughly rinsed with demineralized water, and finally, with deionized water to ensure that all traces of acid and other contaminants were removed. The reactor was then thoroughly dried and charged with the appropriate amounts of monomer mixture comprising para, para-PPPBP (13.02 grams), BPA (9.24 grams), and BMSC (25 grams). The mole ratio of BMSC to the sum of moles of BPA and para, para-PPPBP is 1.03:1. The reactor was then mounted in a polymerization assembly and checked to ensure that no leaks were present. The catalyst solution (200 microliters of a solution containing 5 ppm concentration of sodium hydroxide and 150 ppm of tetramethylammonium hydroxide) was then introduced into the reactor using a syringe. The atmosphere inside the reactor was then evacuated using a vacuum source and purged with nitrogen. This cycle was repeated 3 times after which the contents of the reactor were heated to melt the monomer mixture. After softening the monomer mixture at 200° C. for 10 minutes, the stirrer in the reactor was turned on and adjusted to 50 RPM to ensure the homogeneity of the melt mix. A clear colorless liquid resulted after the softened melt was kept at 210° C. for 10 minutes. Then the temperature of the melt was raised to 220 C and maintained for 10 minutes. Next the temperature was increased to 250° C. and the internal pressure was slowly reduced to 100 millibars. Caution must be observed at this step since a vigorous reaction with foaming is likely. The pressure is carefully reduced to 100 millibars. After maintaining at this condition for 15 minutes, the temperature was raised to 310° C. and then the pressure is brought down to about 1 millibar. After being maintained at

TABLE 6

| Example Number | Metal oxide (weight percent) | Solvent | T (° C.) | Average values of metal levels (ppb | | | | | |
|---|---|---|---|---|---|---|---|---|---|
| | | | | Fe | Ca | Na | Al | Zn | APHA |
| Control-3 | NA | NA | NA | 11424 | 1158 | 461 | 1354 | 248 | 13 |
| E-23 | Acidic Silica (20) | 80/20 acetone/water | Ambient | 219 | 319 | 430 | 185 | <20 | NA |
| E-24 | Acidic Silica (10) | 90/10 IPA/water | Ambient | 810 | 493 | 281 | 644 | 110 | NA |
| E-25 | Acidic Silica (10) | 80/20 acetone/water | Ambient | 320 | 329 | 535 | 69 | 575 | NA |
| E-26 | Acidic Silica (10) | IPA | 75 | 522 | 279 | 426 | 452 | 65 | 4 |
| E-27 | Modified Acidic Silica (10) | IPA | 75 | 359 | 199 | 289 | 32 | <10 | 5 |
| E-28 | Acidic alumina | 90/10 IPA/water | Ambient | 392 | 382 | 186 | 382 | 116 | 5 |

The results shown in Table 6 illustrate that metal oxides such as silica and acidic alumina are effective in removing metals such as iron, calcium, sodium, aluminum, and zinc to less than 500 ppb and furnishing para, para-PPPBP having APHA color values of less than 10.

this condition for 10 minutes, the polycarbonate was isolated by breaking the glass nipple at the bottom of the reactor and collecting the product. In the case where the product polycarbonate had a high molecular weight, the hot molten polymer was dropped down by pressurizing the reactor with nitrogen gas. The results are shown in Table 7. Polydispersity (PDI) is given by the ratio of the weight average molecular weight ($M_w$) to the number average molecular weight ($M_n$).

In comparative Example 7 (CE-7), the PPPBP comonomer used was the sample prepared as described Example 1. In Example 29, pure para, para-PPPBP having less than 50 ppm of AP impurity was used. In Example 30, an ultra-pure para, para-PPPBP purified using acidic alumina as the metal oxide adsorbent was used.

TABLE 7

| Example Number | PPPBP Comonomer | Mw | Mn | PDI | Delta YI |
|---|---|---|---|---|---|
| CE-7 | para, para-PPPBP | 33,388 | 14,356 | 2.32 | 23.4 |
| 29 | Pure para, para-PPPBP | 53,892 | 23,765 | 2.27 | 2.3 |
| 30 | Ultra-pure para, para-PPPBP | 53,710 | 24,637 | 2.18 | 1.8 |

The data for Comparative Example 7 and Example 29 shows that when the AP impurity is removed from para, para-PPPBP to less than 50 ppm, the YI of the polycarbonate copolymer decreases drastically from 23.4 to 2.3. Further, Examples 29 and 30 show that when trace levels of metals, such as iron are removed from a pure para, para-PPPBP, there is a further significant reduction in the YI of the polycarbonate copolymer.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this invention, but that the disclosure will include all embodiments falling within the scope of the appended claims.

The invention claimed is:

1. A method for purifying a 2-aryl-3,3-bis(hydroxyaryl) phthalimidine compound, the method comprising:
contacting a crude 2-aryl-3,3-bis(hydroxyaryl)phthalimidine compound with a solid acidic material, an organic acid chloride, an organic anhydride, a solution of a mineral acid in a polar organic solvent, a solution of an organosulfonic acid having 2 or more carbon atoms in an organic solvent, acetic acid, or a combination thereof, to remove a 2-aryl-3-(aminoaryl)-3-(hydroxyaryl)phthalimidine compound having a formula:

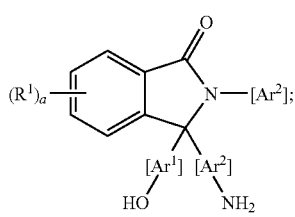

wherein each $R^1$ is independently selected from the group consisting of a hydrocarbyl radical, a nitro radical, and a halogen atom; "a" is an integer from 0 to 4; and $Ar^1$ and $Ar^2$ are independently at each occurrence an aromatic radical; and producing a purified 2-aryl-3,3-bis(hydroxyaryl)phthalimidine product comprising less than 200 parts per million of the 2-aryl-3-(aminoaryl)-3-(hydroxyaryl)phthalimidine compound.

2. The method of claim 1, further comprising treating the purified 2-aryl-3,3-bis(hydroxyaryl)phthalimidine product with a polar organic solvent and reducing an APHA value of the product to less than 20 as measured using test method ASTM D1209.

3. The method of claim 1, wherein the solid acidic material comprises an acidic metal oxide, an acidic organic polymer, or a combination of the acidic metal oxide and the acidic organic polymer.

4. The method of claim 3, wherein the acidic metal oxide comprises an acidic silica, an acidic alumina, an acid-washed carbon, or a sulfated zirconia.

5. The method of claim 3, wherein the acidic organic polymer is selected from the group consisting of a poly(vinylsulfonic acid), a poly(vinylphosphonic acid), and an acidic ion exchange resin.

6. The method of claim 5, wherein the acidic ion exchange resin is a sulfonated polystyrene-divinylbenzene copolymer crosslinked with up to 20 weight percent of divinylbenzene relative to an overall weight of the acidic ion exchange resin.

7. The method of claim 3, wherein the organosulfonic acid having 2 or more carbon atoms is selected from the group consisting of ethanesulfonic acid, propanesulfonic acid, butanesulfonic acid, octanesulfonic acid, dodecylbenzenesulfonic acid, and a combination of the foregoing organosulfonic acids.

8. The method of claim 1, wherein the acid in a polar organic solvent is an alcoholic mineral acid, wherein the mineral acid is selected from the group consisting of phosphoric acid, hydrochloric acid, and a combination of the foregoing mineral acids.

9. The method of claim 1, wherein the organic anhydride is phthalic anhydride.

10. The method of claim 1, further comprising recycling the purification agent, wherein the purification agent is an acidic ion exchange resin.

11. The method of claim 1, further comprising contacting the purified 2-aryl-3,3-bis(hydroxyaryl)phthalimidine product with a metal oxide for a period of time effective to reduce one or more metal impurity concentrations to less than 500 parts per billion of each metal and produce an ultra-pure 2-aryl-3, 3-bis(hydroxyaryl)phthalimidine.

12. The method of claim 11, wherein the metal oxide comprises a basic metal oxide, a neutral metal oxide, or an acidic metal oxide.

13. The method of claim 11, wherein the metal oxide is selected from the group consisting of an acidic silica and an acidic alumina.

14. The method of claim 11, further comprising washing the metal oxide with an aqueous mineral acid prior to contacting the purified 2-aryl-3,3-bis(hydroxyaryl)phthalimidine product with the metal oxide.

15. The method of claim 14, wherein the aqueous mineral acid is hydrochloric acid.

16. The method of claim 11, wherein the one or more metal impurities is selected from the group consisting of iron, calcium, zinc, aluminum, and sodium.

17. The method of claim 1, wherein the 2-aryl-3,3-bis(hydroxyaryl)phthalimidine is 2-phenyl-3,3-bis(4-hydroxyphenyl)phthalimidine.

18. A polymer comprising structural units derived from the purified 2-aryl-3,3-bis(hydroxyaryl)phthalimidine product of claim 1.

19. A polycarbonate comprising structural units derived from the purified 2-aryl-3,3-bis(hydroxyaryl)phthalimidine product of claim 2 and having an APHA value of less than 20 as measured using test method ASTM D1209, and wherein the 2-aryl-3,3-bis(hydroxyaryl)phthalimidine has the structure of formula (I):

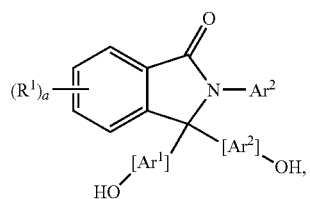

(I)

wherein $R^1$ is independently selected from a group consisting of a hydrocarbyl radical, a nitro radical, and a halogen atom; "a" is an integer from 0-4; and $Ar^1$ and $Ar^2$ are independently at each occurrence an aromatic radical.

20. A method for preparing an ultra-pure 2-aryl-3,3-bis(hydroxyaryl)phthalimidine product, the method comprising:

contacting a 2-aryl-3,3-bis(hydroxyaryl)phthalimidine with a solid acidic material, an organic acid chloride, an organic anhydride, a solution of an acid in a polar organic solvent, a solution of an organosulfonic acid having 2 or more carbon atoms in an organic solvent, acetic acid, or a combination thereof, to produce a purified 2-aryl-3,3-bis(hydroxyaryl)phthalimidine product comprising one or more metal impurities at a concentration of greater than 500 parts per billion of each metal, and less than 200 parts per million of a 2-aryl-3-(aminoaryl)-3-(hydroxyaryl)phthalimidine having a formula:

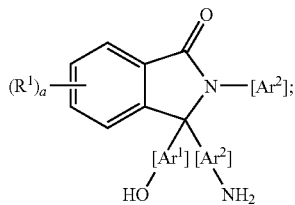

wherein each $R^1$ is independently selected from the group consisting of a hydrocarbyl radical, a nitro radical, and a halogen atom; "a" is an integer from 0 to 4; and $Ar^1$ and $Ar^2$ are independently at each occurrence an aromatic radical; and contacting the purified 2-aryl-3,3-bis(hydroxyaryl)phthalimidine product with a metal oxide adsorbent to produce the ultra-pure 2-aryl-3,3-bis(hydroxyaryl)phthalimidine product wherein at least one of the metal impurities has been reduced to less than 500 parts per billion of the metal.

21. The method of claim 20, further comprising treating the 2-aryl-3,3-bis(hydroxyaryl)phthalimidine with a polar organic solvent prior to contacting with the metal oxide adsorbent, to produce a 2-aryl-3,3-bis(hydroxyaryl)phthalimidine having an APHA value of less than 10 as measured using test method ASTM D1209.

22. A method for preparing a polycarbonate polymer comprising structural units derived from a 2-aryl-3,3-bis(hydroxyaryl)phthalimidine compound, the method comprising:

reacting a 2-aryl-3,3-bis(hydroxyaryl)phthalimidine compound with a carbonate precursor to produce the polycarbonate polymer, wherein the 2-aryl-3,3-bis(hydroxyaryl)phthalimidine compound has less than 200 parts per million of a 2-aryl-3-(aminoaryl)-3-(hydroxyaryl)phthalimidine having a formula:

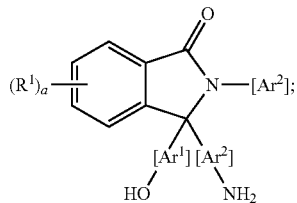

wherein each $R^1$ is independently selected from a group consisting of a hydrocarbyl radical, a nitro radical, and a halogen atom; "a" is an integer from 0 to 4; and $Ar^1$ and $Ar^2$ are independently at each occurrence an aromatic radical.

23. The method of claim 22, wherein the 2-aryl-3,3-bis(hydroxyaryl)phthalimidine compound has less than 500 parts per billion of at least three of iron, calcium, sodium, aluminum, and zinc.

24. The method of claim 22, wherein the 2-aryl-3,3-bis(hydroxyaryl)phthalimidine compound has an APHA value of less than 20 as measured using test method ASTM D1209.

25. The method of claim 22, wherein the polycarbonate has a yellowness index of less than 10 as measured using test method ASTM E313-00.

26. A polycarbonate comprising structural units derived from an ultra-pure 2-phenyl-3,3-bis(4-hydroxyphenyl)phthalimidine product, wherein the ultra-pure 2-phenyl-3,3-bis(4-hydroxyphenyl)phthalimidine product comprises less than 200 parts per million of 2-phenyl-3-(4-aminophenyl)-3-(4-hydroxyphenyl)phthalimidine; and less than 500 parts per billion of at least three of iron, calcium, sodium, aluminum, and zinc individually.

27. The method of claim 16, wherein the 2-aryl-3,3-bis(hydroxyaryl)phthalimidine compound has less than 500 parts per billion of each of iron, calcium, sodium, aluminum, and zinc individually.

28. The method of claim 20, wherein the 2-aryl-3,3-bis(hydroxyaryl)phthalimidine compound has less than 500 parts per billion of each of iron, calcium, sodium, aluminum, and zinc individually.

29. The method of claim 22, wherein the 2-aryl-3,3-bis(hydroxyaryl)phthalimidine compound has less than 500 parts per billion of each of iron, calcium, sodium, aluminum, and zinc individually.

30. The polycarbonate of claim 26, wherein the 2-phenyl-3,3-bis(4-hydroxyphenyl)phthalimidine compound has less than 500 parts per billion of each of iron, calcium, sodium, aluminum, and zinc individually.

* * * * *